(12) United States Patent
Draghia-Akli

(10) Patent No.: US 7,361,642 B2
(45) Date of Patent: Apr. 22, 2008

(54) CANINE SPECIFIC GROWTH HORMONE RELEASING HORMONE

(75) Inventor: Ruxandra Draghia-Akli, The Woodlands, TX (US)

(73) Assignee: VGX Pharmaceuticals, Inc., Blue Bell, PA (US)

( * ) Notice: Subject to any disclaimer, the term of this patent is extended or adjusted under 35 U.S.C. 154(b) by 0 days.

(21) Appl. No.: 10/894,644

(22) Filed: Jul. 20, 2004

(65) Prior Publication Data

US 2005/0032737 A1 Feb. 10, 2005

Related U.S. Application Data

(60) Provisional application No. 60/492,427, filed on Aug. 4, 2003.

(51) Int. Cl.
*A61K 31/70* (2006.01)

(52) U.S. Cl. .................. 514/44; 514/12; 530/300; 530/311; 530/324; 435/320.1; 435/69.1

(58) Field of Classification Search .................... None
See application file for complete search history.

(56) References Cited

U.S. PATENT DOCUMENTS

| | | |
|---|---|---|
| 4,223,019 A | 9/1980 | Momany |
| 4,223,020 A | 9/1980 | Momany |
| 4,223,021 A | 9/1980 | Momany |
| 4,224,316 A | 9/1980 | Momany |
| 4,226,857 A | 10/1980 | Momany |
| 4,228,156 A | 10/1980 | Momany |
| 4,228,158 A | 10/1980 | Momany |
| 4,410,512 A | 10/1983 | Bowers |
| 4,833,166 A | 5/1989 | Grosvenor |
| 4,839,344 A | 6/1989 | Bowers |
| 4,956,288 A | 9/1990 | Barsoum |
| 5,023,322 A | 6/1991 | Kovacs |
| 5,036,045 A | 7/1991 | Thorner |
| RE33,699 E | 9/1991 | Drengler |
| 5,061,690 A | 10/1991 | Kann |
| 5,084,442 A | 1/1992 | Felix |
| 5,134,120 A | 7/1992 | Boyd |
| 5,137,872 A | 8/1992 | Seely |
| 5,292,721 A | 3/1994 | Boyd |
| 5,439,440 A | 8/1995 | Hoffman |
| 5,486,505 A | 1/1996 | Bowers |
| 5,605,885 A | 2/1997 | Bernton |
| 5,696,089 A | 12/1997 | Felix |
| 5,702,304 A | 12/1997 | Acres |
| 5,704,908 A | 1/1998 | Hoffman |
| 5,756,264 A | 5/1998 | Schwartz |
| 5,776,901 A | 7/1998 | Bowers |
| 5,792,747 A | 8/1998 | Schally |
| 5,846,936 A | 12/1998 | Felix |
| 5,847,066 A | 12/1998 | Coy |
| 5,872,127 A | 2/1999 | Cincotta |
| 6,551,996 B1 | 4/2003 | Schwartz |
| 2004/0057941 A1* | 3/2004 | Draghia-Akli et al. ... 424/93.21 |
| 2005/0064554 A1* | 3/2005 | Fisher et al. ............... 435/69.4 |

FOREIGN PATENT DOCUMENTS

| | | |
|---|---|---|
| EP | 1205551 | 5/2002 |
| WO | WO 95/19805 | 7/1995 |
| WO | WO 96/12006 | 4/1996 |
| WO | WO 96/12520 | 5/1996 |
| WO | WO 97/07826 | 3/1997 |
| WO | WO 2004 007678 | 1/2004 |
| WO | WO 2004 108761 | 12/2004 |

OTHER PUBLICATIONS

Wells, Biochemistry 29: 8509-8517, 1990.*
European Patent Office, International Search Report and Written Opinion, dated Aug. 16, 2005.
U.S. Appl. No. 60/396,247, filed Jul. 16, 2002.
Acsadi, G., G. Dickson, D. R. Love, A. Jani, F. S. Walsh, A. Gurusinghe, Wolff, JA, and K. E. Davies. 1991. Human dystrophin expression in mdx mice after intramuscular injection of DNA constructs. Nature 352:815-818.
Aihara, H. and J. Miyazaki. 1998. Gene transfer into muscle by electroporation in vivo. Nat. Biotechnol. 16:867-870.
Aratani, Y., R. Okazaki, and H. Koyama. 1992. End extension repair of introduced targeting vectors mediated by homologous recombination in mammalian cells. Nucleic Acids Res. 20:4795-4801.
Bettan, M., F. Emmanuel, R. Darteil, J. M. Caillaud, F. Soubrier, P. Delaere, D. Branelec, A. Mahfoudi, N. Duverger, and D. Scherman. 2000. High-level protein secretion into blood circulation after electric pulse-mediated gene transfer into skeletal muscle. Mol. Ther. 2:204-210.
Butler, A. A., G. R. Ambler, B. H. Breier, D. LeRoith, C. T. Roberts, Jr., and P. D. Gluckman. 1994. Growth hormone (GH) and insulin-like growth factor-1 (IGF-1) treatment of the GH-deficient dwarf rat: differential effects on IGF-I transcription start site expression in hepatic and extrahepatic tissues and lack of effect on type I IGF receptor mRNA expression. Mol. Cell Endocrinol. 101:321-330.
Caroni, P. and C. Schneider. 1994. Signaling by insulin-like growth factors in paralyzed skeletal muscle: rapid induction of IGF1 expression in muscle fibers and prevention of interstitial cell proliferation by IGF-BF5 and IGF-BP4. J. Neurosci. 14:3378-3388.
Corpas, E., S. M. Harman, M. A. Pineyro, R. Roberson, and M. R. Blackman. 1993. Continuous subcutaneous infusions of growth hormone (GH) releasing hormone 1-44 for 14 days increase GH and insulin-like growth factor-I levels in old men. Journal of Clinical Endocrinology & Metabolism 76:134-138.

(Continued)

*Primary Examiner*—Robert S. Landsman
*Assistant Examiner*—Gyan Chandra
(74) *Attorney, Agent, or Firm*—Pepper Hamilton, LLP

(57) ABSTRACT

A composition and a method of increasing growth hormone ("GH") values in a canine or dog, and more specifically, a canine- or dog-specific growth hormone releasing hormone ("dGHRH"), or functional biological equivalent thereof. The dGHRH is an isolated composition or a nucleic acid molecule that encodes the dGHRH or functional biological equivalent. Also, a method for delivering the composition of this invention to a subject, wherein the dGHRH increases the level of growth hormone ("GH") secretion in a recipient subject, such as a canine or dog.

9 Claims, 8 Drawing Sheets

OTHER PUBLICATIONS

Danko, I. and J. A. Wolff. 1994. Direct gene transfer into muscle. Vaccine 12:1499-1502.

Davis, H. L., R. G. Whalen, and B. A. Demeneix. 1993. Direct gene transfer into skeletal muscle in vivo: factors affecting efficiency of transfer and stability of expression. Human Gene Therapy 4:151-159.

Dolnik, V., M. Novotny, and J. Chmelik. 1993. Electromigration behavior of poly-(L-glutamate) conformers in concentrated polyacrylamide gels. Biopolymers 33:1299-1306.

Draghia-Akli R, Cummings KK, Khan AS, Brown PA, Carpenter RH. Effects of plasmid-mediated growth hormone releasing hormone supplementation in young, healthy Beagle dogs. J Anim Sci. Sep 2003;81(9):2301-10.

Draghia-Akli, R., K. M. Ellis, L. A. Hill, P. B. Malone, and M. L. Fiorotto. 2003b. High-efficiency growth hormone releasing hormone plasmid vector administration into skeletal muscle mediated by electroporation in pigs. FASEB J 17:526-528.

Draghia-Akli, R., M. L. Fiorotto, L. A. Hill, P. B. Malone, D. R. Deaver, and R. J. Schwartz. 1999. Myogenic expression of an injectable protease-resistant growth hormone-releasing hormone augments long-term growth in pigs. Nat. Biotechnol. 17:1179-1183.

Draghia-Akli, R., K. A. Hahn, G. K. King, K. Cummings, and R. H. Carpenter. 2002a. Effects Of Plasmid Mediated Growth Hormone Releasing Hormone in Severely Debilitated Dogs With Cancer. Molecular Therapy 6:830-836.

Draghia-Akli, R., A. S. Khan, K. K. Cummings, D. Parghi, R. H. Carpenter, and P. A. Brown. 2002b. Electrical Enhancement of Formulated Plasmid Delivery in Animals. Technology in Cancer Research & Treatment 1:365-371.

Draghia-Akli, R., X. G. Li, and R. J. Schwartz. 1997. Enhanced growth by ectopic expression of growth hormone releasing hormone using an injectable myogenic vector. Nat. Biotechnol. 15:1285-1289.

Draghia-Akli, R., P. B. Malone, L. A. Hill, K. M. Ellis, R. J. Schwartz, and J. L. Nordstrom. 2002c. Enhanced animal growth via ligand-regulated GHRH myogenic-injectable vectors. FASEB J. 16:426-428.

Dubreuil, P., D. Petitclerc, G. Pelletier, P. Gaudreau, C. Farmer, Mowles, TF, and P. Brazeau. 1990. Effect of dose and frequency of administration of a potent analog of human growth hormone-releasing factor on hormone secretion and growth in pigs. Journal of Animal Science 68:1254-1268.

Etherton, T. D., et al., 1986. Stimulation of pig growth performance by porcine growth hormone and growth-releasing factor. Journal of Animal Science 63:1389-1399.

Fewell, J. G., et al., 2001. Gene therapy for the treatment of hemophilia B using PINC-formulated plasmid delivered to muscle with electroporation. Mol. Ther. 3:574-583.

Foncea, R., M. et al., 1997. Insulin-like growth factor-I rapidly activates multiple signal transduction pathways in cultured rat cardiac myocytes. J. Biol. Chem. 272:19115-19124.

Frohman, L. A., T. R. Downs, and P. Chomczynski. 1992. Regulation of growth hormone secretion. Frontiers in Neuroendocrinology 13:344-405.

Frohman, L. A., et al., 1984. Metabolic clearance and plasma disappearance rates of human pancreatic tumor growth hormone releasing factor in man. J. Clin. Invest. 73:1304-1311.

Fryer, A. D. and D. B. Jacoby. 1993. Effect of inflammatory cell mediators on M2 muscarinic receptors in the lungs. Life Sci. 52:529-536.

Gehl, J., T. Skovsgaard, and L. M. Mir. 1998. Enhancement of cytotoxicity by electropermeabilization: an improved method for screening drugs. Anticancer Drugs 9:319-325.

Gehl, J., T. H. Sorensen, K. Nielsen, P. Raskmark, S. L. Nielsen, T. Skovsgaard, and L. M. Mir. 1999. In vivo electroporation of skeletal muscle: threshold, efficacy and relation to electric field distribution. Biochim. Biophys. Acta 1428:233-240.

Gesundheit, N. and J. K. Alexander. 1995. Endocrine Therapy with Recombinant Hormones and Growth Factors. In: B. D. Weintraub (Ed.) Molecular Endocrinology: Basic Concepts and Clinical Correlations. pp. 491-507. Raven Press,Ltd., New York.

Heller, R., M. J. Jaroszeski, L. F. Glass, J. L. Messina, D. P. Rapaport, R. C. DeConti, N. A. Fenske, R. A. Gilbert, L. M. Mir, and D. S. Reintgen. 1996. Phase I/II trial for the treatment of cutaneous and subcutaneous tumors using electrochemotherapy. Cancer 77:964-971.

Hoess, R. H. and K. Abremski. 1985. Mechanism of strand cleavage and exchange in the Cre-lox site-specific recombination system. J. Mol. Biol. 181:351-362.

Kooistra, H. S., G. Voorhout, J. A. Mol, and A. Rijnberk. 2000. Combined pituitary hormone deficiency in german shepherd dogs with dwarfism. Domest. Anim Endocrinol. 19:177-190.

Kooistra, H. S., G. Voorhout, P. J. Selman, and A. Rijnberk. 1998. Progestin-induced growth hormone (GH) production in the treatment of dogs with congenital GH deficiency. Domest. Anim Endocrinol. 15:93-102.

Lapierre, H., G. Pelletier, D. Petitclerc, P. Dubreuil, J. Morisset, P. Gaudreau, Y. Couture, and P. Brazeau. 1991. Effect on human growth hormone-releasing factor and(or) thyrotropin-releasing factor of growth, carcass composition, diet digestibility, nutrient balance, and plasma constituents in dairy calves. Journal of Animal Science 69:587-598.

Lesbordes, J. C., T. Bordet, G. Haase, L. Casteinau-Ptakhine, S. Rouhani, H. Gilgenkrantz, and A. Kahn. 2002. In vivo electrotransfer of the cardiotrophin-1 gene into skeletal muscle slows down progression of motor neuron degeneration in pmn mice. Hum. Mol. Genet. 11:1615-1625.

Li, C., S. Ke, Q. P. Wu, W. Tansey, N. Hunter, L. M. Buchmiller, L. Milas, C. Chamsangavej, and S. Wallace. 2000. Tumor irradiation enhances the tumor-specific distribution of poly(L-glutamic acid)-conjugated paclitaxel and its antitumor efficacy. Clin. Cancer Res. 6:2829-2834.

Li, X., E. M. Eastman, R. J. Schwartz, and R. Draghia-Akli. 1999. Synthetic muscle promoters: activities exceeding naturally occurring regulatory sequences. Nat. Biotechnol. 17:241-245.

Liu, J. L. and D. LeRoith. 1999. Insulin-like growth factor I is essential for postnatal growth in response to growth hormone. Endocrinology 140:5178-5184.

Lowe, W. L., Jr., M. Adamo, H. Werner, C. T. Roberts, Jr., and D. LeRoith. 1989. Regulation by fasting of rat insulin-like growth factor I and its receptor. Effects on gene expression and binding. J. Clin. Invest 84:619-626.

Lucas, M. L., L. Heller, D. Coppola, and R. Heller. 2002. IL-12 plasmid delivery by in vivo electroporation for the successful treatment of established subcutaneous B16.F10 melanoma. Mol. Ther. 5:668-675.

Lucas, M. L., M. J. Jaroszeski, R. Gilbert, and R. Heller. 2001. In vivo electroporation using an exponentially enhanced pulse: a new waveform. DNA Cell Biol. 20:183-188.

Matsubara, H., Y. Gunji, T. Maeda, K. Tasaki, Y. Koide, T. Asano, T. Ochiai, S. Sakiyama, and M. Tagawa. 2001. Electroporation-mediated transfer of cytokine genes into human esophageal tumors produces anti-tumor effects in mice. Anticancer Res. 21:2501-2503.

Matsuo, A., I. Tooyama, S. Isobe, Y. Oomura, I. Akiguchi, K. Hanai, J. Kimura, and H. Kimura. 1994. Immunohistochemical localization in the rat brain of an epitope corresponding to the fibroblast growth factor receptor-1. Neuroscience 60:49-66.

McNally, M. A., J. S. Lebokowski, T. B. Okama, and L. B. Lerch. 1988. Optimizing electroporation parameters for a variety of human hematopoietic cell lines. Biotechniques 6:882-886.

Miklavcic, D., K. Beravs, D. Semrov, M. Cemazar, F. Demsar, and G. Sersa. 1998. The importance of electric field distribution for effective in vivo electroporation of tissues. Biophys. J. 74:2152-2158.

Mumper, R. J., J. Wang, S. L. Klakamp, H. Nitta, K, Anwer, F. Tagliaferri, and A. P. Rolland. 1998. Protective interactive noncondensing (PINC) polymers for enhanced plasmid distribution and expression in rat skeletal muscle. J. Control Release 52:191-203.

Muramatsu, T., S. Arakawa, K. Fukazawa, Y. Fujiwara, T. Yoshida, R. Sasaki, S. Masuda, and H. M. Park. 2001. In vivo gene electroporation in skeletal muscle with special reference to the duration of gene expression. Int. J Mol. Med. 7:37-42.

Nairn, R. S., G. M. Adair, T. Porter, S. L. Pennington, D. G. Smith, J. H. Wilson, and M. M. Seidman. 1993. Targeting vector configuration and method of gene transfer influence targeted correction of the APRT gene in Chinese hamster ovary cells. Somat. Cell Mol. Genet. 19:363-375.

Neumann, E., M. Schaefer-Ridder, Y. Wang, and P. H. Hofschneider. 1982. Gene transfer into mouse lyoma cells by electroporation in high electric fields. EMBO J. 1:841-845.

Otani, Y., Y. Tabata, and Y. Ikada. 1996. Rapidly curable biological glue composed of gelatin and poly(L-glutamic acid). Biomaterials 17:1387-1391.

Otani, Y., Y. Tabata, and Y. Ikada. 1998. Hemostatic capability of rapidly curable glues from gelatin, poly(L-glutamic acid), and carbodiimide. Biomaterials 19:2091-2098.

Parks, J. S., R. W. Pfaffle, M. R. Brown, H. Abdul-Latif, and L. R. Meacham. 1995. Growth Hormone Deficiency. In: B. D. Weintraub (Ed.) Molecular Endocrinology: Basic Concepts and Clinical Correlations. pp. 473-490. Raven Press,Ltd., New York.

Parrizas, M. and D. LeRoith. 1997. Insulin-like growth factor-1 inhibition of apoptosis is associated with increased expression of the bcl-xL gene product. Endocrinology 138:1355-1358.

Rabinovsky, E. D., G. M. Smith, D. P. Browder, H. D. Shine, and J. L. McManaman. 1992. Peripheral nerve injury down-regulates CNTF expression in adult rat sciatic nerves. J. Neurosci. Res. 31:188-192.

Rijnberk, A., H. van Herpen, J. A. Mol, and G. R. Rutteman. 1993. Disturbed release of growth hormone in mature dogs: a comparison with congenital growth hormone deficiency. Vet. Rec. 133:542-545.

Smith, L. C. and J. L. Nordstrom. 2000. Advances in plasmid gene delivery and expression in skeletal muscle. Curr. Opin. Mol. Ther. 2:150-154.

Terada, Y., H. Tanaka, T. Okado, S. Inoshita, M. Kuwahara, T. Akiba, S. Sasaki, and F. Marumo. 2001. Efficient and ligand-dependent regulated erythropoietin production by naked dna injection and in vivo electroporation. Am. J Kidney Dis. 38:S50-S53.

Thorner, M. O., L. A. Frohman, D. A. Leong, J. Thominet, T. Downs, P. Hellmann, J. Chitwood, J. M. Vaughan, and W. Vale, 1984. Extrahypothalamic growth-hormone-releasing factor (GRF) secretion is a rare cause of acromegaly: plasma GRF levels in 177 acromegalic patients. Journal of Clinical Endocrinology & Metabolism 59:846-849.

Toneguzzo, F., A. Keating, S. Glynn, and K. McDonald. 1988. Electric field-mediated gene transfer: characterization of DNA transfer and patterns of integration in lymphoid cells. Nucleic Acids Res. 16:5515-5532.

Tripathy, S. K., E. C. Svensson, H. B. Black, E. Goldwasser, M. Margalith, Hobart, PM, and J. M. Leiden. 1996. Long-term expression of erythropoietin in the systemic circulation of mice after intramuscular injection of a plasmid DNA vector, Proc. Natl. Acad. Sci. USA 93:10876-10880.

Tsurumi, Y., S. Takeshita, D. Chen, et al., 1996. Direct intramuscular gene transfer of naked DNA encoding vascular endothelial growth factor augments collateral development and tissue perfusion [see comments]. Circulation 94:3281-3290.

Van Rooij, E. M., B. L. Haagmans, H. L. Glansbeek, et al., 2000. A DNA vaccine coding for glycoprotein B of pseudorabies virus induces cell-mediated immunity in pigs and reduces virus excretion early after infection. Vet. Immunol. Immunopathol. 74:121-136.

Vance, M. L. 1990. Growth-hormone-releasing hormone. [Review] [52 refs.]. Clinical Chemistry 36:415-420.

Vance, M. L., D. L. Kaiser, W. S. Evans, R. Furlanetto, W. Vale, J. Rivier, and M. O. Thorner. 1985. Pulsatile growth hormone secretion in normal man during a continuous 24-hour infusion of human growth hormone releasing factor (1-40). Evidence for intermittent somatostatin secretion. J. Clin. Invest. 75:1584-1590.

Veldhuis, J. D., A. Iranmanesh, and A. Weltman. 1997. Elements In The Pathophysiology Of Diminished Growth Hormone (GH) Secretion In Aging Humans. Endocrine 7:41-48.

Vilquin, J. T., P. F. Kennel, M. Paturneau-Jouas, P. Chapdelaine, N. Boissel, P. Delaere, J. P. Tremblay, D. Scherman, M. Y. Fiszman, and K. Schwartz. 2001. Electrotransfer if naked DNA in the skeletal muscles of animal models of muscular dystrophies. Gene Ther. 8:1097-1107.

Wolff, J. A., R. W. Malone, P. Williams, W. Chong, G. Acsadi, A. Jani, Feigner, adn PL. 1990. Direct gene transfer into mouse muscle in vivo. Science 247:1465-1468.

Xie, T. D. and T. Y. Tsong. 1993. Study of mechanisms of electric field-induced DNA transfection. V. Effects of DNA topology on surface binding, cell uptake, expression, and integration into host chromosomes of DNA in the mammalian cell. Biophys. J. 65:1684-1689.

Yasui, A., K. Oda, H. Usunomiya, K. Kakudo, T. Suzuki, T. Yoshida, H. M. Park, K. Fukazawa, and T. Muramatsu. 2001. Elevated gastrin secretion by in vivo gene electroporation in skeletal muscle. Int. J Mol. Med. 8:489-494.

Yin, D. and J. G. Tang. 2001. Gene therapy for streptozotocin-induced diabetic mice by electroporational tranfer of naked human insulin precursor DNA into skeletal muscle in vivo. FEBS Lett. 495:16-20.

Yorifuji, T. and H. Mikawa. 1990. Co-transfer of restriction endonucleases and plasmid DNA into mammalian cells by electroporation: effects on stable transformation. Mutat. Res. 243:121-126.

\* cited by examiner

Alignment of HV-pGHRH and dog-GHRH (dGHRH) coding sequences

```
            1                                                              60
dog GHRH   (1)  ATGGTGCTCTGGGTGTTCTTCCTGGTGATCCTCACCCTCAGCAGTGGTTCCCACTCTTCC
HV-pGHRH   (1)  ATGGTGCTCTGGGTGTTCTTCTTTGTGATCCTCACCCTCAGCAACAGCTCCCACTGCTCC
Consensus  (1)  ATGGTGCTCTGGGTGTTCTTC T GTGATCCTCACCCTCAGCA    G TCCCACT TCC 61                                                            120
dog GHRH  (61)  CCGCCATCCC---TGCCCATCAGAATCCCTCGGTATGCAGACGCCATCTTCACCAACAGC
HV-pGHRH  (61)  CCACCTCCCCCTTTGACCCTCAGGATGCGGGGGCACGTAGATGCCATCTTCACCAACAGC
Consensus (61)  CC CC  CCC    TG CC TCAG AT C  CGG A G AGA GCCATCTTCACCAACAGC 121                                                           180
dog GHRH (118)  TACCGGAAGGTGCTGGGCCAGCTGTCCGCCCCGCAAGCTCCTSCAGGACATCATGAGCCGG
HV-pGHRH (121)  TACCGGAAGGTGCTGGCCCAGCTGTCCGCCCCGCAAGCTGTCTCCAGGACATCCTGAACAGG
Consensus(121)  TACCGGAAGGTGCTGG  CCAGCTGTCCGCCCCGCAAGCT CT CAGGACATC TGA C GG 181                                                           219
dog GHRH (178)  CAGCAGGGAGAGAGAAACCGGGAGCAAGGAGCATAGTAA
HV-pGHRH (181)  CAGCAGGGAGAGAGAGAACCAAGAGCAAGGAGCATAATGA
Consensus(181)  CAGCAGGGAGAGAG  AACC  GAGCAAGGAGCATA T A
```

Figure 1

Alignment of HV-pGHRH and dog-GHRH (dGHRH) amino acid sequences

```
                1                                                            60
dog GHRH   (1)  MVLWVFFLVILTLSSGSHSSPPS-LPIRIPRYADAIFTNSYRKVLGQLSARKLLQDIMSR
HV-pGHRH   (1)  MVLWVFFFVILTLSNSSHCSPPPPLTLRMRRHVDAIFTNSYRKVLAQLSARKLLQDILNR
Consensus  (1)  MVLWVFF VILTLS  SH SPP   L IRI RH DAIFTNSYRKVLAQLSARKLLQDIL  R 61         73
dog GHRH  (60)  QQGERNREQGA--
HV-pGHRH  (61)  QQGERNQEQGA--
Consensus (61)  QQGERN EQGA
```

Figure 2 pAV0221 (dog-GHRH plasmid) sequence

```
ccaccgcggt ggcggccgtc cgccctcggc accatcctca cgacacccaa atatggcgac    60
gggtgaggaa tggtggggag ttattttag agcggtgagg aaggtgggca ggcagcaggt    120
gttggcgctc taaaaataac tcccgggagt tatttttaga gcggaggaat ggtggacacc    180
caaatatggc gacggttcct caccgtcgc catatttggg tgtccgccct cggccggggc    240
cgcattcctg ggggccgggc ggtgctcccg cccgcctcga taaaaggctc cggggccggc    300
ggcggcccac gagctacccg gaggagcggg aggcgccaag cggatcccaa ggcccaactc    360
cccgaaccac tcagggtcct gtggacagct caccctagctg ccatggtgct ctgggtgttc    420
ttcctggtga tcctcacccct cagcagtggt tcccactctt ccccgccatc cctgcccatc    480
agaatccctc ggtatgcaga cgccatcttc accaacagct accggaaggt gctgggccag    540
ctgtccgccc gcaagctcct scaggacatc atgagccggc agcagggaga gagaaaccgg    600
gagcaaggag catagtaagc ttatcggggt ggcatccctg tgacccctcc ccagtgcctc    660
tcctggccct ggaagttgcc actccagtgc ccaccagcct tgtcctaata aaattaagtt    720
gcatcatttt gtctgactag gtgtccttct ataatattat ggggtggagg ggggtggtat    780
ggagcaaggg gcaagttggg aagacaacct gtagggctcg agggggggcc cggtaccagc    840
ttttgttccc tttagtgagg gttaatttcg agcttggtct tccgcttcct cgctcactga    900
ctcgctgcgc tcggtcgttc ggctgcggcg agcggtatca gctcactcaa aggcggtaat    960
acggttatcc acagaatcag gggataacgc aggaaagaac atgtgagcaa aaggccagca    1020
aaaggccagg aaccgtaaaa aggccgcgtt gctggcgttt ttccataggc tccgcccccc    1080
tgacgagcat cacaaaaatc gacgctcaag tcagaggtgg cgaaacccga caggactata    1140
aagataccag gcgtttcccc ctggaagctc cctcgtgcgc tctcctgttc cgaccctgcc    1200
gcttaccgga tacctgtccg cctttctccc ttcgggaagc gtggcgcttt ctcatagctc    1260
acgctgtagg tatctcagtt cggtgtaggt cgttcgctcc aagctgggct gtgtgcacga    1320
accccccgtt cagcccgacc gctgcgcctt atccggtaac tatcgtcttg agtccaaccc    1380
ggtaagacac gacttatcgc cactggcagc agccactggt aacaggatta gcagagcgag    1440
gtatgtaggc ggtgctacag agttcttgaa gtggtggcct aactacggct acactagaag    1500
aacagtattt ggtatctgcg ctctgctgaa gccagttacc ttcggaaaaa gagttggtag    1560
ctcttgatcc ggcaaacaaa ccaccgctgg tagcggtggt ttttttgttt gcaagcagca    1620
gattacgcgc agaaaaaaag gatctcaaga agatcctttg atcttttcta cggggtctga    1680
cgctcagcta gctctcagaa gaactcgtca agaaggcgat agaaggcgat gcgctgcgaa    1740
tcgggagcgg cgataccgta agcacgagg aagcggtcag cccattcgcc gcaagctct    1800
tcagcaatat cacgggtagc caacgctatg tcctgatagc ggtccgccac acccagccgg    1860
ccacagtcga tgaatccaga aaagcggcca ttttccacca tgatattcgg caagcaggca    1920
tcgccatgag tcacgacgag atcctcgccg tcgggcatgc gcgccttgag cctggcgaac    1980
agttcggctg gcgcgagccc ctgatgctcg tcgtccagat catcctgatc gacaagaccg    2040
gcttccatcc gagtacgtgc tcgctcgatg cgatgtttcg cttggtggtc gaatgggcag    2100
gtagccggat caagcgtatg cagccgccgc attgcatcag ccatgatgga tactttctcg    2160
gcaggagcaa ggtgagatga caggagatcc tgccccggca cttcgcccaa tagcagccag    2220
tcccttcccg cttcagtgac aacgtcgagc acagctgcgc aaggaacgcc cgtcgtggcc    2280
agccacgata gccgcgctgc ctcgtcctgc agttcattca gggcaccgga caggtcggtc    2340
ttgacaaaaa gaaccgggcg cccctgcgct gacagccgga acacggcggc atcagagcag    2400
ccgattgtct gttgtgccca gtcatagccg aatagcctct ccacccaagc ggccggagaa    2460
cctgcgtgca atccatcttg ttcaatcatg cgaaacgatc ctcatcctgt ctcttgatca    2520
gatcttgatc ccctgcgcca tcagatcctt ggcggcaaga agccatcca gtttactttg    2580
cagggcttcc caaccttacc agagggcgcc ccagctggca attccggttc gcttgctgtc    2640
cataaaaccg cccagtctag caactgttgg aagggcgat cgtgtaatac gactcactat    2700
agggcgaatt ggagct                                                    2716
```

Figure 3 pAV0215 (HV-GHRH plasmid) sequence

```
ccaccgcggt ggcggccgtc cgccctcggc accatcctca cgacacccaa atatggcgac    60
gggtgaggaa tggtggggag ttatttttag agcggtgagg aaggtgggca ggcagcaggt   120
gttggcgctc taaaaataac tcccgggagt tatttttaga gcggaggaat ggtggacacc   180
caaatatggc gacggttcct cacccgtcgc catatttggg tgtccgccct cggccggggc   240
cgcattcctg ggggccgggc ggtgctcccg cccgcctcga taaaaggctc cggggccggc   300
ggcggccac gagctacccg gaggagcggg aggcgccaag cggatcccaa ggcccaactc   360
cccgaaccac tcagggtcct gtggacagct cacctagctg ccatggtgct ctgggtgttc   420
ttctttgtga tcctcaccct cagcaacagc tcccactgct ccccacctcc ccctttgacc   480
ctcaggatgc ggcggcacgt agatgccatc ttcaccaaca gctaccggaa ggtgctggcc   540
cagctgtccg cccgcaagct gctccaggac atcctgaaca ggcagcaggg agagaggaac   600
caagagcaag gagcataatg actgcaggaa ttcgatatca agcttatcgg ggtggcatcc   660
ctgtgacccc tccccagtgc ctctcctggc cctggaagtt gccactccag tgcccaccag   720
ccttgtccta ataaaattaa gttgcatcat tttgtctgac taggtgtcct tctataatat   780
tatggggtgg aggggggtgg tatggagcaa ggggcaagtt gggaagacaa cctgtagggc   840
tcgagggggg gcccggtacc agcttttgtt ccctttagtg agggttaatt tcgagcttgg   900
tcttccgctt cctcgctcac tgactcgctg cgctccgtcg ttcggctgcg gcgagcggta   960
tcagctcact caaaggcggt aatacggtta tccacagaat caggggataa cgcaggaaag  1020
aacatgtgag caaaaggcca gcaaaaggcc aggaaccgta aaaaggccgc gttgctggcg  1080
ttttttccata ggctccgccc cctgacgag catcacaaaa atcgacgctc aagtcagagg  1140
tggcgaaacc cgacaggact ataaagatac caggcgtttc ccctggaag ctccctcgtg  1200
cgctctcctg ttccgaccct gccgcttacc ggatacctgt ccgcctttct cccttcggga  1260
agcgtggcgc tttctcatag ctcacgctgt aggtatctca gttcggtgta ggtcgttcgc  1320
tccaagctgg gctgtgtgca cgaaccccc gttcagcccg accgctgcgc cttatccggt  1380
aactatcgtc ttgagtccaa cccggtaaga cacgacttat cgccactggc agcagccact  1440
ggtaacagga ttagcagagc gaggtatgta ggcggtgcta cagagttctt gaagtggtgg  1500
cctaactacg gctacactag aagaacagta tttggtatct gcgctctgct gaagccagtt  1560
accttcggaa aaagagttgg tagctcttga tccggcaaac aaaccaccgc tggtagcggt  1620
ggtttttttg tttgcaagca gcagattacg cgcagaaaaa aaggatctca agaagatcct  1680
ttgatctttt ctacggggtc tgacgctcag ctagcgctca gaagaactcg tcaagaaggc  1740
gatagaaggc gatgcgctgc gaatcggag cggcgatacc gtaaagcacg aggaagcggt  1800
cagcccattc gccgccaagc tcttcagcaa tatcacgggt agccaacgct atgtcctgat  1860
agcggtccgc cacacccagc cggccacagt cgatgaatcc agaaaagcgg ccattttcca  1920
ccatgatatt cggcaagcag gcatcgccat gagtcacgac gagatcctcg ccgtcgggca  1980
tgcgcgcctt gagcctggcg aacagttcgg ctggcgcgag ccctgatgc tcttcgtcca  2040
gatcatcctg atcgacaaga ccggcttcca tccgagtacg tgctcgctcg atgcgatgtt  2100
tcgcttggtg gtcgaatggg caggtagccg gatcaagcgt atgcagccgc cgcattgcat  2160
cagccatgat ggatactttc tcggcaggag caaggtgaga tgacaggaga tcctgccccg  2220
gcacttcgcc caatagcagc cagtcccttc ccgcttcagt gacaacgtcg agcacagctg  2280
cgcaaggaac gcccgtcgtg gccagccacg atagccgcgc tgcctcgtcc tgcagttcat  2340
tcagggcacc ggacaggtcg gtcttgacaa aagaaccgg gcgcccctgc gctgacagcc  2400
ggaacacggc ggcatcagag cagccgattg tctgttgtgc ccagtcatag ccgaatagcc  2460
tctccaccca agcggccgga gaacctgcgt gcaatccatc ttgttcaatc atgcgaaacg  2520
atcctcatcc tgtctcttga tcagatcttg atcccctgcg ccatcagatc cttggcggca  2580
agaaagccat ccagtttact ttgcagggct tcccaacctt accagagggc gccccagctg  2640
gcaattccgg ttcgcttgct gtccataaaa ccgcccagtc tagcaactgt tgggaagggc  2700
gatcgtgtaa tacgactcac tatagggcga attggagct                          2739
```

Figure 4

CANINE SPECIFIC GROWTH HORMONE RELEASING HORMONE

RELATED APPLICATIONS

This application claims priority to U.S. Provisional Patent Application, Ser. No. 60/492,427, entitled "Canine Specific Growth Hormone Releasing Hormone," filed on Aug. 4, 2003, having Draghia-Akli, listed as the inventor, the entire content of which is hereby incorporated by reference.

BACKGROUND

This invention pertains to an isolated composition and a method of increasing growth hormone ("GH") values in a canine or dog. More specifically, the invention pertains to a canine- or dog-specific growth hormone releasing hormone ("dGHRH"), or functional biological equivalent thereof. The dGHRH is an isolated composition or a nucleic acid molecule that encodes the dGHRH or functional biological equivalent. Another aspect of the current invention includes a method for delivering the composition of this invention to a subject, wherein the dGHRH increases the level of growth hormone ("GH") secretion in a recipient subject, such as a canine or dog.

In the United States, the companion canine population is about 60 million. Although not wanting to be bound by theory, the average lifespan for these canines has increased in recent decades due to better nutrition, and better health care options. Even though the average disease profile and lifespan of the canine population are generally breed specific, there are common disease related features and age related features that are present in most mammals. For example, as mammals age, the GHRH-GH-IGF-I axis undergoes considerable decrement, with reduced GH secretion and IGF-I production associated with a loss of skeletal muscle mass (sarcopenia), osteoporosis, increased fat deposition, decreased lean body mass, and other disorders. Studies in humans and other mammals have demonstrated that the development of these changes can be offset by recombinant growth hormone ("GH") therapy. One benefit of the claimed invention is observed when a dog specific growth hormone releasing hormone ("dGHRH") composition is delivered to a canine subject and the level of GH secretion in the canine subject is increased. Another aspect of the current invention is the dGHRH molecule or functional biological equivalent thereof. The composition may also be a nucleic acid molecule that encodes the dGHRH or functional biological equivalent thereof. The dGHRH can be defined as a biologically active polypeptide that has been engineered to contain a distinct amino acid sequence having similar or improved biologically activity when compared to a generic GHRH ("GHRH") polypeptide. Other benefits from administering the dGHRH compound to the canine subject are outlined in preferred embodiments and include: increased insulin-like growth factor I ("IGF-I"), increased red blood cells production and hemoglobin concentration, and improved protein metabolism.

In humans and other mammals, regulated expression of the GH pathway is considered essential for optimal linear growth, as well as homeostasis of carbohydrate, protein, and fat metabolism. GH synthesis and its pulsatile secretion from the anterior pituitary is stimulated by GHRH and inhibited by somatostatin, both hypothalamic hormones (Frohman et al., 1992). GH increases production of insulin-like growth factor-I ("IGF-I") primarily in the liver, as well as other target organs. IGF-I and GH feedback on the hypothalamus and pituitary to inhibit GHRH release and GH secretion. The endogenous rhythm of GH secretion becomes entrained to the imposed rhythm of exogenous GHRH (Caroni and Schneider, 1994).

Although not wanting to be bound by theory, the linear growth velocity and body composition of humans, farm animals, and companion animals appear to respond to GH or GHRH replacement therapies under a broad spectrum of conditions. Similarly, anemia associated with different diseases and conditions can be treated by physiologically stimulating the GHRH axis (Draghia-Akli et al., 2002a; Draghia-Akli et al., 2003a). However, the etiology of these conditions can vary significantly. For example, in 50% of human GH deficiencies the GHRH-GH-IGF-I axis is functionally intact, but does not elicit the appropriate biological responses in its target tissues. Similar phenotypes are produced by genetic defects at different points along the GH axis (Parks et al., 1995), as well as in non-GH-deficient short stature. In humans, these non-GH-deficiency causes of short stature, such as Turner syndrome (Butler et al., 1994), hypochondroplasia (Foncea et al., 1997), Crohn's disease (Parrizas and LeRoith, 1997), intrauterine growth retardation (Hoess and Abremski, 1985) or chronic renal insufficiency (Lowe, Jr. et al., 1989) can be efficiently treated with GHRH or GH therapy (Gesundheit and Alexander, 1995). In companion animals, such as dogs, there is little or no available therapy, and recombinant protein therapies have proved to be inefficient (Kooistra et al., 1998; Kooistra et al., 2000; Rijnberk et al., 1993).

In aging mammals, the GHRH-GH-IGF-I axis undergoes considerable decrement having reduced GH secretion and IGF-I production associated with a loss of skeletal muscle mass (sarcopenia), osteoporosis, increased fat deposition and decreased lean body mass (Caroni and Schneider, 1994; Veldhuis et al., 1997). It has been demonstrated that the development of these changes can be offset by recombinant GH therapy. GH replacement therapy both in children and the elderly is widely used clinically. Current GH therapy has several shortcomings, however, including frequent subcutaneous or intravenous injections, insulin resistance and impaired glucose tolerance (Rabinovsky et al., 1992); children are also vulnerable to premature epiphyseal closure and slippage of the capital femoral epiphysis (Liu and LeRoith, 1999). A "slow-release" form of GH (from Genentech) has been developed that only requires injections every 14 days. However, this GH product appears to perturb the normal physiological pulsatile GH profile, and is also associated with frequent side effects.

Various GH and GHRH regimens are also available for use in domestic livestock. For example, administration of GHRH and GH stimulate milk production, with an increase in feed to milk conversion. This therapy enhances growth primarily by increasing lean body mass (Lapierre et al., 1991; van Rooij et al., 2000) with overall improvement in feed efficiency. Hot and chilled carcass weights are increased and carcass lipid (percent of soft-tissue mass) is decrease by administration of GHRH and GH (Etherton et al., 1986).

Administering novel GHRH analog proteins (U.S. Pat Nos. 5,847,066; 5,846,936; 5,792,747; 5,776,901; 5,696,089; 5,486,505; 5,137,872; 5,084,442; 5,036,045; 5,023,322; 4,839,344; 4,410,512, RE33,699), synthetic or naturally occurring peptide fragments of GHRH (U.S. Pat. Nos. 4,833,166; 4,228,158; 4,228,156; 4,226,857; 4,224,316; 4,223,021; 4,223,020; 4,223,019) for the purpose of increasing release of GH have been reported. A GHRH analog containing the following mutations has been reported (U.S.

Pat. No. 5,846,936): Tyr at position 1 to His; Ala at position 2 to Val, Leu, or others; Asn at position 8 to Gln, Ser, or Thr; Gly at position 15 to Ala or Leu; Met at position 27 to Nle or Leu; and Ser at position 28 to Asn. The GHRH analog is the subject of U.S. Pat. No. 6,551,996 ("the '996 Patent"), issued on Apr. 22, 2003 having Schwartz et al., listed as inventors. The '996 Patent teaches application of a GHRH analog containing mutations that improve the ability to elicit the release of GH. In addition, the '996 patent relates to the treatment of growth deficiencies; the improvement of growth performance; the stimulation of production of GH in an animal at a greater level than that associated with normal growth; and the enhancement of growth utilizing the administration of GH releasing hormone analog and is herein incorporated by reference.

Studies in humans, sheep or pigs showed that continuous infusion with recombinant GHRH protein restores the normal GH pattern without desensitizing GHRH receptors or depleting GH supplies as this system is capable of feed-back regulation, which is abolished in the GH therapies (Dubreuil et al., 1990; Vance, 1990; Vance et al., 1985). Although GHRH protein therapy stimulates normal cyclical GH secretion with virtually no side effects (Corpas et al., 1993), the short half-life of the molecule in vivo requires frequent (e.g. one to three times per day) intravenous, subcutaneous or intranasal administrations at about a 300-fold higher dose. Thus, recombinant GHRH administration is not practical as a chronic therapy. However, extracranially secreted GHRH, as a mature or a truncated polypeptide, is often biologically active (Thorner et al., 1984) and a low level of serum GHRH (100 pg/ml) stimulates GH secretion (Corpas et al., 1993). These characteristics make GHRH an excellent candidate for plasmid mediated supplementation of a gene product.

Transgene Delivery and in vivo Expression: Although not wanting to be bound by theory, the delivery of specific transgenes to somatic tissue to correct inborn or acquired deficiencies and imbalances is possible. Such transgene-based drug delivery offers a number of advantages over the administration of recombinant proteins. These advantages include: the conservation of native protein structure; improved biological activity; avoidance of systemic toxicities; and avoidance of infectious and toxic impurities. Because the protein is synthesized and secreted continuously into the circulation, plasmid mediated therapy allows for prolonged production of the protein in a therapeutic range. In contrast, the primary limitation of using recombinant protein is the limited availability of protein after each administration.

In a plasmid-based expression system, a non-viral transgene vector may comprise of a synthetic transgene delivery system in addition to the nucleic acid encoding the therapeutic genetic product. In this way, the risks associated with the use of most viral vectors can be avoided, including the expression of viral proteins that can induce immune responses against target tissues and the possibility of DNA mutations or activations of oncogenes. The non-viral expression vector products generally have low toxicity due to the use of "species-specific" components for gene delivery, which minimizes the risks of immunogenicity generally associated with viral vectors. Additionally, no integration of plasmid sequences into host chromosomes has been reported in vivo to date, so that this type of nucleic acid vector therapy should neither activate oncogenes nor inactivate tumor suppressor genes. As episomal systems residing outside the chromosomes, plasmids have defined pharmacokinetics and elimination profiles, leading to a finite duration of gene expression in target tissues.

Direct plasmid DNA gene transfer is currently the basis of many emerging nucleic acid therapy strategies and does not require viral components or lipid particles (Aihara and Miyazaki, 1998; Muramatsu et al., 2001). Skeletal muscle is target tissue, because muscle fiber has a long life span and can be transduced by circular DNA plasmids that are expressed in immunocompetent hosts (Davis et al., 1993; Tripathy et al., 1996). Plasmid DNA constructs are attractive candidates for direct therapy into the subjects skeletal muscle because the constructs are well-defined entities that are biochemically stable and have been used successfully for many years (Acsadi et al., 1991; Wolff et al., 1990). The relatively low expression levels of an encoded product that are achieved after direct plasmid DNA injection are sometimes sufficient to indicate bio-activity of secreted peptides (Danko and Wolff, 1994; Tsurumi et al., 1996). Previous reports demonstrated that human GHRH cDNA could be delivered to muscle by an injectable myogenic expression vector in mice where it transiently stimulated GH secretion to a modest extent over a period of two weeks (Draghia-Akli et al., 1997).

Efforts have been made to enhance the delivery of plasmid DNA to cells by physical means including electroporation, sonoporation, and pressure. Although not wanting to be bound by theory, the administration of a nucleic acid construct by electroporation involves the application of a pulsed electric field to create transient pores in the cellular membrane without causing permanent damage to the cell, which allows exogenous molecules to enter the cell (Smith and Nordstrom, 2000). By adjusting the electrical pulse generated by an electroporetic system, nucleic acid molecules can travel through passageways or pores in the cell that are created during the procedure. U.S. Pat. No. 5,704,908 describes an electroporation apparatus for delivering molecules to cells at a selected location within a cavity in the body of a patient. Similar pulse voltage injection devices are also described in U.S. Pat. Nos. 5,439,440 and 5,702,304, and PCT WO 96/12520, 96/12006, 95/19805, and 97/07826, which are hereby incorporated by reference.

Recently, significant progress to enhance plasmid delivery in vivo and subsequently to achieve physiological levels of a secreted protein was obtained using the electroporation technique. Electroporation has been used very successfully to transfect tumor cells after injection of plasmid (Lucas et al., 2002; Matsubara et al., 2001)) or to deliver the anti-tumor drug bleomycin to cutaneous and subcutaneous tumors in humans (Gehl et al., 1998; Heller et al., 1996). Electroporation also has been extensively used in mice (Lesbordes et al., 2002; Lucas et al., 2001; Vilquin et al., 2001), rats (Terada et al., 2001; Yasui et al., 2001), and dogs (Fewell et al., 2001) to deliver therapeutic genes that encode for a variety of hormones, cytokines or enzymes. Previous studies using GHRH showed that plasmid therapy with electroporation is scalable and represents a promising approach to induce production and regulated secretion of proteins in large animals and humans (Draghia-Akli et al., 1999; Draghia-Akli et al., 2002c). Electroporation also has been extensively used in rodents and other small animals (Bettan et al., 2000; Yin and Tang, 2001). It has been observed that the electrode configuration affects the electric field distribution, and subsequent results (Gehl et al., 1999; Miklavcic et al., 1998). Although not wanting to be bound by theory, needle electrodes give consistently better results than external caliper electrodes in a large animal model.

The ability of electroporation to enhance plasmid uptake into the skeletal muscle has been well documented. Similarly, plasmids formulated with poly-L-glutamate ("PLG")

or polyvinylpyrrolidone ("PVP") were observed to have an increase in plasmid transfection, which consequently increased the expression of a desired transgene. For example, plasmids formulated with PLG or PVP were observed to increase gene expression to up to 10 fold in the skeletal muscle of mice, rats, and dogs (Fewell et al., 2001; Mumper et al., 1998). Although not wanting to be bound by theory, the anionic polymer sodium PLG enhances plasmid uptake at low plasmid concentrations and reduces any possible tissue damage caused by the procedure. PLG is a stable compound and it is resistant to relatively high temperatures (Dolnik et al., 1993). PLG has been used to increase stability of anti-cancer drugs (Li et al., 2000) and as "glue" to close wounds or to prevent bleeding from tissues during wound and tissue repair (Otani et al., 1996; Otani et al., 1998). PLG has been used to increase stability in vaccine preparations (Matsuo et al., 1994) without increasing their immunogenicity. PLG also has been used as an anti-toxin after antigen inhalation or exposure to ozone (Fryer and Jacoby, 1993).

Although not wanting to be bound by theory, PLG increases the transfection of the plasmid during the electroporation process, not only by stabilizing the plasmid DNA and facilitating the intracellular transport through the membrane pores, but also through an active mechanism. For example, positively charged surface proteins on the cells could complex the negatively charged PLG linked to plasmid DNA through protein-protein interactions. When an electric field is applied, the surface proteins reverse direction and actively internalize the DNA molecules, a process that substantially increases the transfection efficiency. Furthermore, PLG will prevent the muscle damage associated with in vivo plasmid delivery (Draghia-Akli et al., 2002b) and will increase plasmid stability in vitro prior to injection. There are studies directed to electroporation of eukaryotic cells with linear DNA (McNally et al., 1988; Neumann et al., 1982) (Toneguzzo et al., 1988) (Aratani et al., 1992; Nairn et al., 1993; Xie and Tsong, 1993; Yorifuji and Mikawa, 1990), but these examples illustrate transfection into cell suspensions, cell cultures, and the like, and such transfected cells are not present in a somatic tissue.

U.S. Pat. No. 4,956,288 is directed to methods for preparing recombinant host cells containing high copy number of a foreign DNA by electroporating a population of cells in the presence of the foreign DNA, culturing the cells, and killing the cells having a low copy number of the foreign DNA.

Although not wanting to be bound by theory, a GHRH cDNA can be delivered to muscle of mice and humans by an injectable myogenic expression vector where it can transiently stimulate GH secretion over a period of two weeks (Draghia-Akli et al., 1997). This injectable vector system was optimized by incorporating a powerful synthetic muscle promoter (Li et al., 1999) coupled with a novel protease-resistant GHRH molecule with a substantially longer half-life and greater GH secretory activity (pSP-HV-GHRH) (Draghia-Akli et al., 1999). Highly efficient electroporation technology was optimized to deliver the nucleic acid construct to the skeletal muscle of an animal (Draghia-Akli et al., 2002b). Using this combination of vector design and electric pulses plasmid delivery method, the inventors were able to show increased growth and favorably modified body composition in pigs (Draghia-Akli et al., 1999; Draghia-Akli et al., 2003b) and rodents (Draghia-Akli et al., 2002c). The modified GHRH nucleic acid constructs increased red blood cell production in companion animals with cancer and cancer treatment-associated anemia (Draghia-Akli et al., 2002a). In pigs, available data suggested that the modified porcine HV-GHRH was more potent in promoting growth and positive body composition changes than the wild-type porcine GHRH (Draghia-Akli et al., 1999). One aspect of the current invention describes a species-specific dGHRH expression vector that comprises a more efficient composition to increase red blood cell production in a canine subject than the protease resistant HV-GHRH molecule.

SUMMARY

Although the average disease profile and lifespan of the canine population are generally breed specific, there are common disease related features and age related features that are present in most mammals. Studies in mammals have demonstrated that the development of hematological changes can be offset by recombinant growth hormone ("GH") therapy. The current invention comprises compositions and methods for increasing GH values in canines.

One aspect of the current invention comprises a canine or dog specific growth hormone releasing hormone ("dGHRH") or functional biological equivalent thereof. In one specific embodiment, the dGHRH or functional biological equivalent increases growth hormone ("GH") when delivered into a subject. The delivered dGHRH or functional biological equivalent thereof improves hematological parameters in the subject, wherein the hematological parameters comprise: red blood cell count, hemoglobin concentration, and mean corpuscular hemoglobin.

Another aspect of the current invention comprises a nucleic acid expression construct encoding the dGHRH or functional biological equivalent thereof. In a second specific embodiment, the dGHRH or functional biological equivalent increases GH when expressed in the subject. The expressed dGHRH or functional biological equivalent thereof improves hematological parameters in the subject, wherein the hematological parameters comprise: red blood cell count, hemoglobin concentration, and mean corpuscular hemoglobin. In a third specific embodiment, the nucleic acid expression construct further comprises: a synthetic or eukaryotic promoter; a poly-adenylation signal; a selectable marker gene promoter; a ribosomal binding site; a selectable marker gene sequence; and an origin of replication. In such an arrangement, the synthetic or eukaryotic promoter, the nucleic acid sequence encoding the dGHRH or functional biological equivalent thereof, and the poly adenylation signal comprise therapeutic elements of the nucleic acid expression construct. The therapeutic elements are operatively linked and located in a first operatively-linked arrangement. Similarly, the selectable marker gene promoter, the ribosomal binding site, the selectable marker gene sequence, and the origin of replication comprise the replication elements of the nucleic acid expression vector and are operatively linked and located in a second operatively-linked arrangement. The first-operatively-linked arrangement and the second-operatively-linked arrangement comprise a circular structure of the nucleic acid expression construct, which is utilized for plasmid mediated gene supplementation. Examples of dGHRH nucleic acid expression constructs of this invention include plasmids pAV0221 and pAV00215.

Still another aspect of the current invention is a method of increasing GH values in a subject. The method comprises delivering into the subject a recombinant dGHRH or functional biological equivalent thereof. The recombinant dGHRH comprises a biologically active polypeptide, and the recombinant functional biological equivalent of dGHRH comprises a polypeptide that has been engineered to contain a distinct amino acid sequence while simultaneously having similar or improved biologically activity when compared to the dGHRH polypeptide. The increasing GH values are related by increasing hematological parameters in the subject having the delivered recombinant dGHRH or functional biological equivalent thereof.

Yet another aspect of the current invention is a method of increasing GH values in a subject. The method comprises delivering into the cells of a subject a nucleic acid expression construct that expresses the dGHRH or functional biological equivalent thereof. In a fourth specific embodiment, the nucleic acid expression construct is delivered into the cells of the subject via an electroporation method. The cells receiving the nucleic acid expression construct comprise somatic cells, stem cells, or germ cells. The dGHRH or functional biological equivalent thereof is expressed in tissue specific cells of the subject (e.g. muscle cells). Examples of nucleic acid expression constructs used for this method include plasmids pAV0221 and pAV00215. In a fifth specific embodiment, the method for delivering the dGHRH nucleic acid expression further comprises using a transfection-facilitating polypeptide, wherein the transfection-facilitating polypeptide comprises a charged polypeptide (e.g. poly-L-glutamate). Increasing GH values are reflected by increasing hematological parameters in the subject having the delivered recombinant dGHRH or functional biological equivalent thereof.

BRIEF DESCRIPTION OF FIGURES

FIG. 1 shows the alignment of HV-GHRH coding sequence, SEQ ID NO:18, and the dGHRH coding sequence, SEQ ID NO:17, and the consensus sequence, SEQ ID NO:19;

FIG. 2 shows alignment of HV-GHRH amino acid sequence, SEQ ID NO:21, and the dGHRH amino acid sequence, SEQ ID NO:20, and the consensus sequence, SEQ ID NO:22; notice that the 5' signal peptide contains 30 amino acids in the dog specific sequence, and it contains 31 amino acids in the HV-GHRH, a modified porcine GHRH with long serum half-life;

FIG. 3 shows the nucleotide sequence of the pAV0221 plasmid vector (SEQ ID NO.: 5) containing the dGHRH sequence;

FIG. 4 shows the nucleotide sequence of the pAV0215 plasmid vector (SEQ ID NO.: 6) containing the HV-GHRH sequence;

DETAILED DESCRIPTION OF PREFERRED EMBODIMENTS

Figure 5:
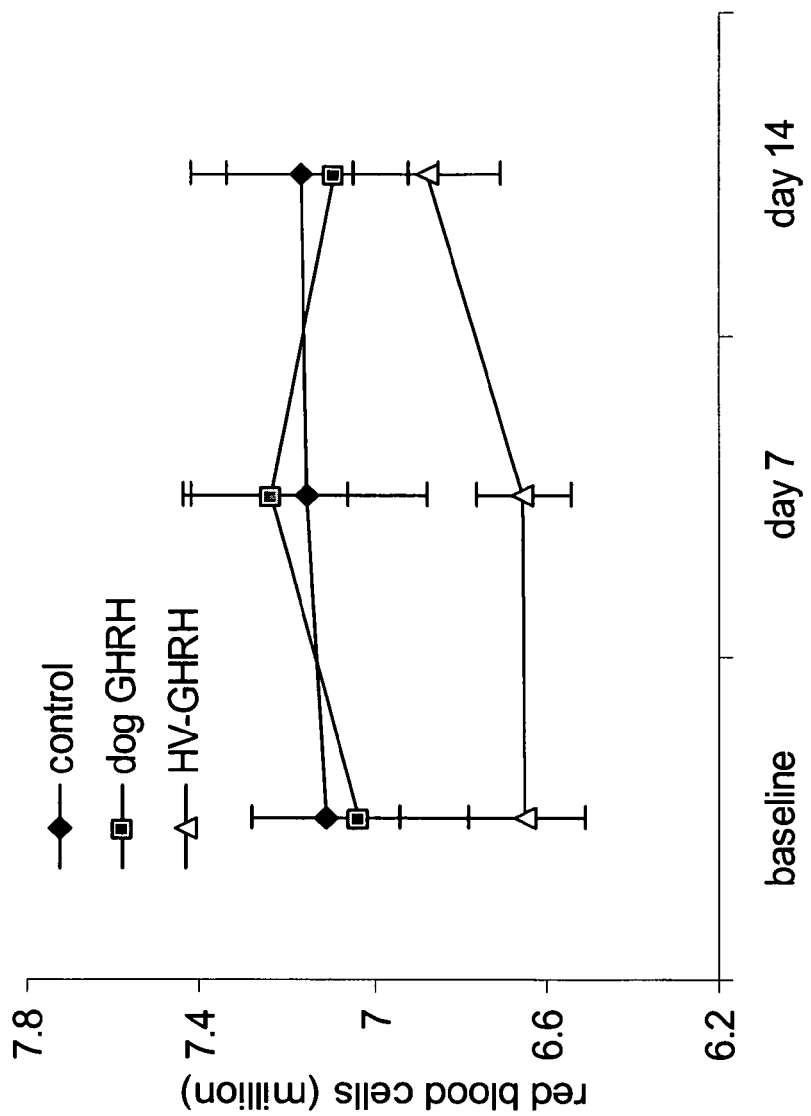
FIG. 5 shows the average red blood cell count in dogs treated with the species specific dGHRH versus controls and dogs treated with the modified porcine HV-GHRH (day 7, P<0.05 versus baseline in dogs treated with dGHRH)

Terms:

The term "analog" as used herein includes any mutant of GHRH, or synthetic or naturally occurring peptide fragments of GHRH.

The terms "canine" and "dog" as used interchangeably herein.

The term "codon" as used herein refers to any group of three consecutive nucleotide bases in a given messenger RNA molecule, or coding strand of DNA that specifies a particular amino-acid, or a starting or stopping signal for translation. The term codon also refers to base triplets in a DNA strand.

The term "coding region" as used herein refers to any portion of the DNA sequence that is transcribed into messenger RNA (mRNA) and then translated into a sequence of amino acids characteristic of a specific polypeptide.

The term "delivery" as used herein is defined as a means of introducing a material into a subject, a cell or any recipient, by means of chemical or biological process, injection, mixing, electroporation, sonoporation, or combination thereof, either without or under pressure.

The term "encoded GHRH" as used herein is a biologically active polypeptide.

The term "functional biological equivalent" of GHRH as used herein is a polypeptide that has been engineered to contain a distinct amino acid sequence while simultaneously having similar or improved biological activity when compared to the GHRH polypeptide.

The term "growth hormone" ("GH") as used herein is defined as a hormone that relates to growth and acts as a chemical messenger to exert its action on a target cell.

The term "growth hormone releasing hormone" ("GHRH") as used herein is defined as a hormone that facilitates or stimulates release of GH, and to a lesser extent other pituitary hormones, such as prolactin.

The term "heterologous nucleic acid sequence" as used herein is defined as a DNA sequence consisting of differing regulatory and expression elements.

The term "isolated" as used herein refers to synthetic or recombinant preparation of molecules in a purified, or concentrated, or both, form, substantially free from undesirable properties.

The term "modified GHRH" as used herein is a polypeptide that has been engineered to contain an amino acid sequence that is distinct from the wild-type GHRH polypeptide while simultaneously having similar or improved biologically activity when compared to the wild-type GHRH polypeptide. The wild-type GHRH polypeptide is the naturally occurring species-specific GHRH polypeptide of a subject, a cell or any recipient of the modified GHRH.

The term "nucleic acid expression construct" as used herein refers to any type of genetic construct comprising a nucleic acid coding for a RNA capable of being transcribed. The transcribed RNA is then capable of being translated into a peptide, polypeptide, or protein. The term "expression vector" or "expression plasmid" can also be used interchangeably.

The term "recipient subject" as used herein refers to a subject that receives a treatment or composition.

The term "subject" as used herein refers to any species of the animal kingdom, including humans. In preferred embodiments it refers more specifically to canines.

The term "domesticated animal" as used herein refers to animals used for: pets (e.g. cats, dogs, etc.); work (e.g. horses, cows, etc.); food (chicken, fish, lambs, pigs, etc); and all others known in the art.

The term "operatively linked" as used herein refers to elements or structures in a nucleic acid sequence that are linked by operative ability and not physical location. The elements or structures are capable of, or characterized by accomplishing a desired operation. It is recognized by one of ordinary skill in the art that it is not necessary for elements or structures in a nucleic acid sequence to be in a tandem or adjacent order to be operatively linked.

The term "promoter" as used herein refers to a sequence of DNA that directs the transcription of a gene. A promoter may direct the transcription of a prokaryotic or eukaryotic gene. A promoter may be "inducible", initiating transcription in response to an inducing agent or, in contrast, a promoter may be "constitutive", whereby an inducing agent does not regulate the rate of transcription. A promoter may be regulated in a tissue-specific or tissue-preferred manner, such that it is only active in transcribing the operable linked coding region in a specific tissue type or types.

The term "replication element" as used herein comprises nucleic acid sequences that will lead to replication of a plasmid in a specified host. One skilled in the art of molecular biology will recognize that the replication element may include, but is not limited to, a selectable marker gene promoter, a ribosomal binding site, a selectable marker gene sequence, and an origin of replication.

The term "therapeutic element" as used herein comprises nucleic acid sequences that will lead to an in vivo expression of an encoded gene product. One skilled in the art of molecular biology will recognize that the therapeutic element may include, but is not limited to a promoter sequence, a poly [A] sequence, or a 3' or 5' UTR.

The term "vector" as used herein refers to any vehicle that delivers a nucleic acid into a cell or organism. Examples include plasmid vectors, viral vectors, liposomes, or cationic lipids.

The standard one and three letter abbreviations for amino acids used herein are as follows: Alanine, A ala; Arginine, R, arg; Asparagine, N, asn; Aspartic acid, D, asp; Cysteine, C, cys; Glutamine, Q, gln; Glutamic acid, E, glu; Glycine, G, gly; Histidine, H, his; Isoleucine, I, ile; Leucine, L, leu; Lysine, K, lys; Methionine, M, met; Phenylalanine, F, phe; Proline, P, pro; Serine, S, ser; Threonine, T, thr; Tryptophan, W, trp; Tyrosine, Y, tyr; Valine, V, val.

In a preferred embodiment, the nucleic acid construct or vector of the present invention is a plasmid that comprises a synthetic myogenic (muscle-specific) promoter, a synthetic nucleotide sequence encoding a dGHRH or its analog, and a 3' untranslated region (3'UTR).

Promoters and Enhancers. A "promoter" is a control sequence that is a region of a nucleic acid sequence at which the initiation and rate of transcription are controlled. It may contain genetic elements where regulatory proteins and molecules may bind such as RNA polymerase and transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one of naturally-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™. Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous. In a specific embodiment the promoter is a synthetic myogenic promoter (Seq. ID No. 11).

The identity of tissue-specific promoters or elements, as well as assays to characterize their activity, is well known to those of skill in the art. Examples of such regions include the human LIMK2 gene, the somatostatin receptor 2 gene, murine epididymal retinoic acid-binding gene, human CD4, mouse alpha2 (XI) collagen, D1A dopamine receptor gene, insulin-like growth factor II, human platelet endothelial cell adhesion molecule-1.

Initiation Signals and Internal Ribosome Binding Sites. A specific initiation signal also may be required for efficient translation (synthesis of the encoded protein) of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, internal ribosome entry sites ("IRES") elements are used to create multigene, or polycistronic messages. IRES elements are able to bypass the ribosome scanning model of 5' methylated Cap-dependent translation and begin translation at internal sites. IRES elements from two members of the picornavirus family (polio and encephalomyocarditis) have been described, as well a IRES from a mammalian message. IRES elements can be linked to heterologous open reading frames. Multiple open reading frames can be transcribed together, each separated by a IRES, creating polycistronic messages. By virtue of the IRES element, each open reading frame is accessible to ribosomes for efficient translation. Multiple genes can be efficiently expressed using a single promoter/enhancer to transcribe a single message.

Multiple Cloning Sites. Vectors can include a multiple cloning site ("MCS"), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing Sites. Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression.

Polvadenvlation Signals. In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the bovine or human GH polyadenylation signal, convenient and/or known to function well in various target cells. In a specific embodiment the polyadenylation signal is a fragment of the 3'UTR of human growth hormone (Seq. ID No. 12). Also contemplated as an element of the expression cassette is a transcriptional termination site. These elements can serve to enhance message levels and/or to minimize read through from the cassette into other sequences.

Origins of Replication. In order to propagate a vector in a host cell, it may contain one or more origins of replication sites (often termed "ori"), which is a specific nucleic acid sequence at which replication is initiated. In a specific embodiment the origin of replication is the pUC-18 origin of replication (Seq. ID No. 16). Alternatively an autonomously replicating sequence ("ARS") can be employed if the host cell is yeast.

Selectable and Screenable Markers. In certain embodiments of the invention, the cells that contain the nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker, such as the antibiotic resistance gene on the plasmid constructs (such as kanamycin, ampicylin, gentamycin, tetracycline, or chloramphenicol). initiated. In a specific embodiment the selectable marker is the kanamycin resistance marker (Seq. ID No. 15).

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

GHRH: GHRH has a short half-life in the circulatory system in mammals (Frohman et al., 1984). The HV-GHRH super-analog was presented in the U.S. patent application Ser. No. 10/021,403 filed on Dec. 12, 2001 and titled "Administration of nucleic acid sequence to female animal to enhance growth in offspring" with Schwartz, et al., listed as inventors and U.S. Pat. No. 6,551,996 ("the '996 Patent"), issued on Apr. 22, 2003 having Schwartz et al., listed as inventors. The '996 Patent teaches application of a GHRH analog containing mutations that improve the ability to elicit the release of GH. In addition, the '996 patent relates to the treatment of growth deficiencies; the improvement of growth performance; the stimulation of production of GH in an animal at a greater level than that associated with normal growth; and the enhancement of growth utilizing the administration of GH releasing hormone analog and is herein incorporated by reference. In order to clone the dGHRH, a dog hypothalamic library was generated and screened.

The invention may be better understood with reference to the following examples, which are representative of some of the embodiments of the invention, and are not intended to limit the invention.

EXAMPLE 1

DNA/Plasmid constructs: GHRH cDNA constructs were introduced into the pAV plasmid backbone, as described in U.S. patent application Ser. No.: 60/396,247 filed on Jul. 16, 2002 and titled "Codon Optimized Synthetic Plasmids" with Draghia-Akli, et al., listed as inventors. Each of the expression vector elements were operatively linked and incorporated into the myogenic GHRH expression vectors. For example, the biological potency of the dGHRH was tested using the pAV plasmid vector that was engineered to direct high levels of skeletal muscle-specific gene expression with the use of a synthetic muscle promoter, SPc5-12 (Li et al., 1999) and a 225-bp fragment of dGHRH, which encodes the 30 amino acid signal peptide and a form of the mature peptide dGHRH (Tyr1-Gly40) followed by the 3' untranslated region of the human GH ("hGH"). The sequence of the muscle specific synthetic promoter (Seq. ID No. 11) and the sequence of the fragment of 3'UTR of human growth hormone (Seq. ID No. 12) are included. Other constructs included the modified porcine HV-GHRH, which was used as a positive control, or another functional biological equivalent thereof. The wild type and mutated porcine GHRH cDNAs were generated by site directed mutagenesis of GHRH cDNA (Altered Sites II in vitro Mutagenesis System, Promega, Madison, Wis.), and cloned into the BamHI/Hind III sites of pSPc5-12, to generate pSP-wt-GHRH, or pSP-TI-GHRH respectively. The 3' untranslated region (3'UTR) of GH was cloned downstream of GHRH cDNA. Each of the resultant plasmids contained a coding region for either a wild type or a mutated form of GHRH. Although not wanting to be bound by theory, some of the mutated resultant amino acid sequences were not naturally present in mammals.

Dog GHRH cloning—A custom cDNA library was constructed by Clontech Laboratories, Inc., Palo Alto, Calif. The starting tissue for the library was dog hypothalamus (4.7 gm) which had been collected from dogs kept in a closed, experimental facility (NIH Regulations) from birth to death and stored at –80° C. The cDNA library was screened by PCR using a 5' primer selected from the Bam/Hind III fragment of HV-GHRH and a 3' primer selected from sequence in Exon 5 of bovine GHRH.

```
Bam/Hind III
5' Primer:
ATG GTG CTC TGG GTG TTC TT    Seq ID No. 07

Exon 5
3' Primer:
TTC ATC CTT GGG AGT TCC TG    Seq ID No. 08
```

PCR conditions were as following: DNA (library) 3 μl, 10×Accutaq buffer 5 μl, DMSO 1 μl, dNTP's (10 mM) 1 μl, Exon3-5'primer (50 ng) 1 μl, Exon 5-3'primer (50 ng) 1 μl, water 37.5 μl, Accutaq 0.5 μl, with the following cycling parameters: 94° C. 10 min, 94° C. 30 sec, 55° C. 30 sec, 68° C. 30 sec for 35 cycles, followed by a cycle at 68° C. for 5 min.

The PCR fragment generated, approx. 200 bp, was subcloned using the TOPO cloning kit and sent for sequencing. Clone #13 was found to be complete and aligned and compared with other GHRH sequences, as that of human GHRH.

Primers were designed with specific mutations to incorporate a restriction sites to facilitate sub-cloning into expression vectors: NcoI, Hind III sites and 2 stop codons in clone #13 for insertion into the new pAV backbone. The newly generated expected band size is approx. 240 bp.

```
dogHindIII B
5' Primer
CGGCCGAAAGCTTACTATGCTCCT    Seq ID No. 09 dogNcoI B
3' Primer
ATTCGCCCCCATGGTGCTCTGGG     Seq ID No. 10
```

PCR Conditions were as following: DNA (clone #13) 10 ng, 10×Accutaq buffer 5 μl, DMSO 1 μl, dNTP's (10 mM) 1 μl, 5' primer (50 ng) 1 μl, 3'primer (50 ng) 1 μl, water 40.5 μl, Accutaq 0.5 μl. The cycling parameters were as following: 95° C. for 3' min, 94° C. 30 sec, 52° C. 30 sec, 68° C. 30 sec, for 30 cycles, followed by on extension at 68° C. for 5 min.

PCR reaction mix digested with NcoI and HindIII and ligated into the new backbone using Takara ligase; clones were then sequenced to confirm that restriction sites and stop codons had been incorporated. Muscle cells (Sol 8's) were transfected with the resulting vector and a Northern blot confirmed presence of species specific RNA.

An alignment of the HV-GHRH and dGHRH coding sequences is shown in FIG. 1, and an alignment of the corresponding amino acid sequences is shown in FIG. 2. As shown below, the encoded GHRH amino acid sequences are different:

Porcine (pGHRH):

```
                                              SEQ ID NO. 01
YADAIFTNSYRKVLGQLSARKLLQDIMSRQQGERNQEQGA-OH
```

Mutated porcine (HV-GHRH):

```
                                              SEQ ID NO. 02
HVDAIFTNSYRKVLAQLSARKLLQDILNRQQGERNQEQGA-OH
```

Canine or Dog specific (dGHRH):

```
                                              SEQ ID NO. 03
YADAIFTNSYRKVLGQLSARKLLQDIMSRQQGERNREQGA-OH
```

Although not wanting to be bound by theory, the effects of treating a GH deficient diseases or anemia is determined ultimately by the circulating levels of needed hormones. In general, the encoded dGHRH or functional biological equivalent thereof is of formula:

```
                                              SEQ ID NO. 04
X₁X₂DAIFTNSYRKVLX₃QLSARKLLQDIX₄X₅RQQGERNREQGA
``` wherein: $X_1$ is a D- or L-isomer of an amino acid selected from the group consisting of tyrosine ("Y"), or histidine ("H"); $X_2$ is a D- or L-isomer of an amino acid selected from the group consisting of alanine ("A"), valine ("V"), or isoleucine ("I"); $X_3$ is a D- or L-isomer of an amino acid selected from the group consisting of alanine ("A") or glycine ("G"); $X_4$ is a D- or L-isomer of an amino acid selected from the group consisting of methionine ("M"), or leucine ("L"); $X_5$ is a D- or L-isomer of an amino acid selected from the group consisting of serine ("S") or aspargines ("N").

The pAV0221 plasmid shown in FIG. 3 and SeqID No. 05 comprises a coding region for the dGHRH. The pAV0215 plasmid shown in FIG. 4 and SeqID No. 06 comprises a coding region for the mutated HV-GHRH. The plasmids described above do not contain polylinker, IGF-I gene, a skeletal alpha-actin promoter or a skeletal alpha actin 3' UTR/NCR. Furthermore, these plasmids were introduced by muscle injection, followed by in vivo electroporation, as described below.

In terms of "functional biological equivalents", it is well understood by the skilled artisan that, inherent in the definition of a "biologically functional equivalent" protein and/or polynucleotide, is the concept that there is a limit to the number of changes that maybe made within a defined portion of the molecule while retaining a molecule with an acceptable level of equivalent biological activity. Functional biological equivalents are further defined herein as those proteins (and polynucleotides) in selected amino acids (or codons) may be substituted. A peptide comprising a functional biological equivalent of a species specific GHRH is a polypeptide that has been engineered to contain distinct amino acid sequences while simultaneously having similar or improved biologically activity when compared to GHRH. For example one biological activity of GHRH is to facilitate GH secretion in the subject. Another example of a functional biological equivalent is a biologically active peptide or nucleic acid sequence having at least 95% identity to any of the corresponding SeqID No's.: 1-10.

EXAMPLE 2

Experimental animals: Nine dogs were divided into three groups of 3 animals. All dogs were of approximately the same age (±1-2 months), at least 1 year-old, and weight within 5% of each other. Group I received water for injection on day 1 and constitute the negative control group. Group II received 1 mg dog-GHRH plasmid on day 1 and constitute the test group. Group III received 1 mg HV-GHRH plasmid on day 1 and constitute the positive control group. Plasmid formulation or water for injection was administered by intramuscular injection followed by electroporation on Day 1. Blood samples for measurement of hematology, serum chemistry and hormone parameters were collected during physical exams on Day -6 and on Day 1 prior to dosing. Additional blood collections were done every following week to the end of the study. Urine was collected and urinalysis performed on Day 1 prior to dosing and at termination of the study for each animal. Injection sites (medial thigh) were examined for signs of erythema and edema during physical examinations, at dosing on Day 1, Day 2 and every week thereafter. The following hematological parameters were measured at the indicated time points: erythrocyte counts ("RBC"), hematocrit, hemoglobin, total leukocyte count ("WBC"), and differential leukocyte counts (neutrophils, lymphocytes, monocytes, eosinophils, and basophils), platelet count, MCV, MCH, MCHC.

Red blood cell production. As shown in FIG. 5, the dog group that was treated with the plasmid encoding the dGHRH (□) showed an increase (P<0.05) in red blood cell count as soon as day 7 post-injection when compared to baseline values. By comparison, the dogs treated with the plasmid encoding the modified porcine HV-GHRH (Δ) molecule, which was proved to stimulate hematopoiesis long-term post-injection, did not show any improvement in their day 7 hematological parameters.

Figure 6:
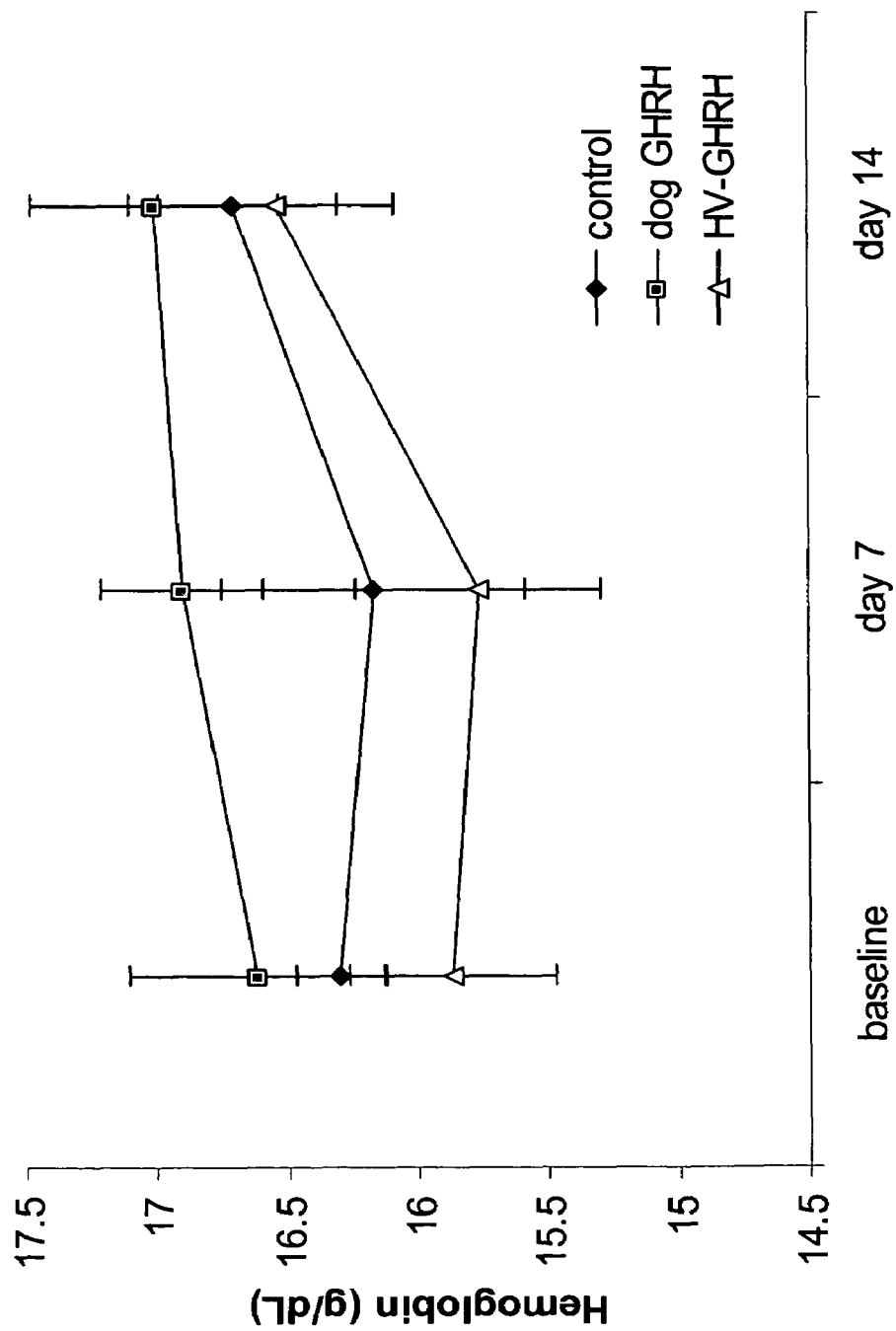
FIG. 6 shows the average hemoglobin in dogs treated with the species specific dGHRH versus controls and dogs treated with the modified porcine HV-GHRH (day 14, P<0.05 versus baseline in dogs treated with dGHRH)
Figure 7:
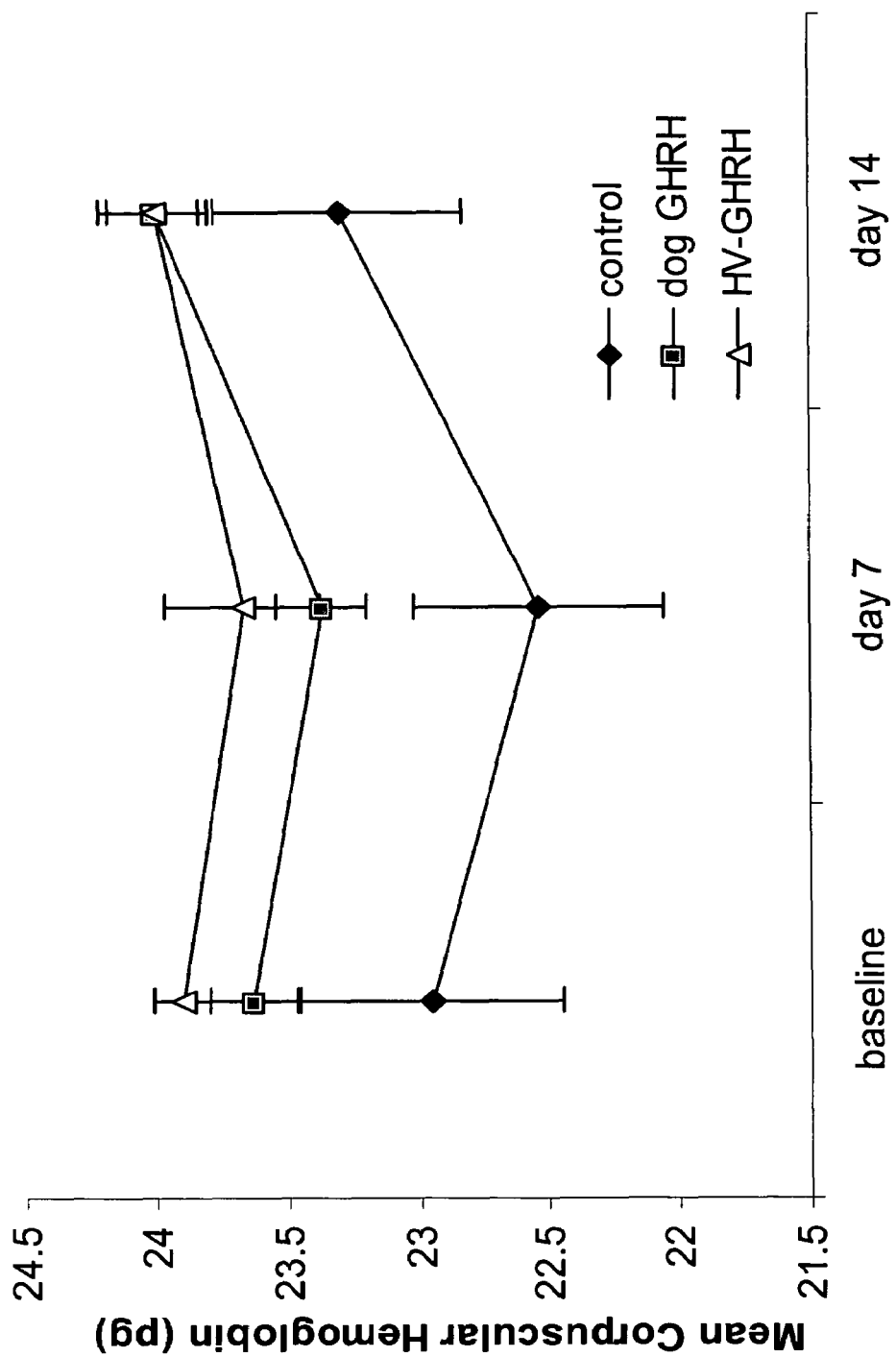
FIG. 7 shows the average mean corpuscular hemoglobin in dogs treated with the species specific dGHRH versus controls and dogs treated with the modified porcine HV-GHRH (day 14, P<0.01 versus baseline in dogs treated with dGHRH)
Figure 8:
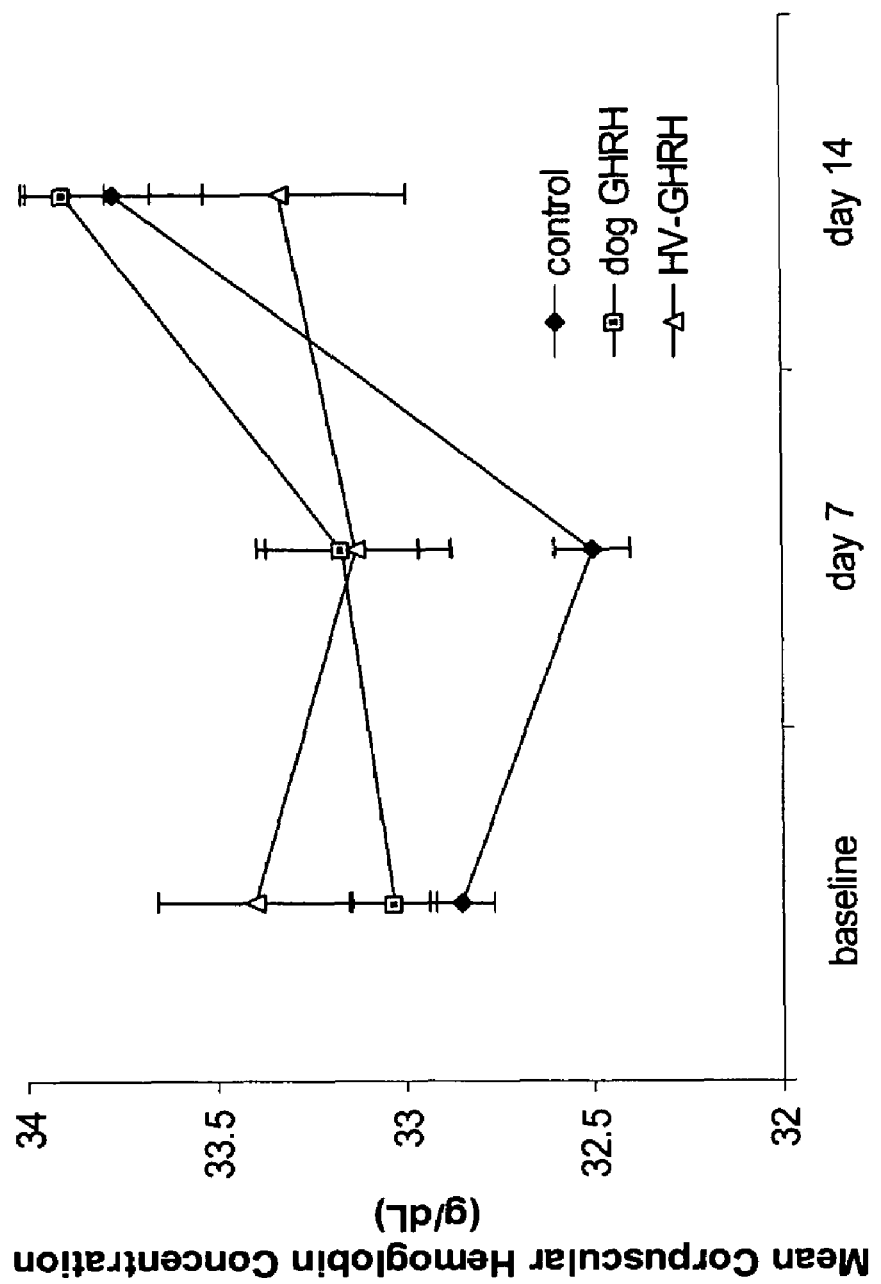
FIG. 8 shows the average mean corpuscular hemoglobin concentration in dogs treated with the species specific dGHRH versus controls and dogs treated with the modified porcine HV-GHRH (day 14, P<0.002 versus baseline in dogs treated with dGHRH).

Hemoglobin production. As shown in FIG. 6, the Beagle dogs that were injected with the plasmid encoding the dGHRH (□) showed an increase in the production of hemoglobin (P<0.05) at 14 days post-injection. Additionally, the mean corpuscular hemoglobin for the Beagle dogs that were injection with the plasmid encoding the dGHRH (□) was also increased (P<0.01), as shown in FIG. 7. The mean corpuscular hemoglobin concentration increased when compared to baseline values in the dog group treated with the plasmid encoding dGHRH (P<0.002), as shown in FIG. 8. In contrast, the dogs treated with the plasmid encoding the modified porcine HV-GHRH (Δ) molecule, which was proved to stimulate hematopoiesis long-term post-injection, did not show any improvement in their hematological parameters.

Although not wanting to be bound by theory, regulatory hormones (e.g. GHRH and GH) often contain a complex feedback-regulated pathway, which are further complicated by chronic conditions (e.g. cancer, immunodeficiency syndromes, and others). Without direct experimentation of the GHRH or biological equivalents that are used in plasmid mediated supplementation, a beneficial therapy could not be predicted by one skilled in the art to determine what modifications to the encoded GHRH or it's functional biological equitant will yield a desired result. For example, previous experiments have indicated that the modified mammalian HV-GHRH produced desired affects faster than the porcine wild-type GHRH (Draghia-Akli et al., 1999). As shown in the example described above, the dGHRH improved canine hematological parameters faster and more efficiently than the modified mammalian HV-GHRH. The invention described herein contains the compositions, descriptions, and results of essential experimentation that explored species specific of distinctive nucleic acid sequences that encoded for a dGHRH or biological equivalent thereof, which was not obvious based upon prior art.

One skilled in the art readily appreciates that the disclosed invention is well adapted to carry out the mentioned and inherent objectives. GH, GHRH, modified growth hormone releasing hormone or functional biological equivalents, plasmids, vectors, pharmaceutical compositions, treatments, methods, procedures and techniques described herein are presented as representative of the preferred embodiments and are not intended as limitations of the scope of the invention. Thus, other uses will occur to those skilled in the art that are encompassed within the spirit and scope of the described invention.

The entire content of each of the following documents and publications are hereby incorporated by reference.

| No. | Number | Date | Inventor |
|---|---|---|---|
| U.S. PATENT DOCUMENTS | | | |
| 1 | U.S. Ser. No. 60/396,247 | Jul. 16, 2002 | Draghia-Akli |
| 2 | U.S. Pat. No. 6,551,996 | Apr. 22, 2003 | Schwartz |
| 3 | U.S. Pat. No. 5,872,127 | Feb. 16, 1999 | Cincotta |
| 4 | U.S. Pat. No. 5,847,066 | Dec. 8, 1998 | Coy |
| 5 | U.S. Pat. No. 5,846,936 | Dec. 8, 1998 | Felix |
| 6 | U.S. Pat. No. 5,792,747 | Aug. 11, 1998 | Schally |
| 7 | U.S. Pat. No. 5,776,901 | Jul. 7, 1998 | Bowers |
| 8 | U.S. Pat. No. 5,756,264 | May 26, 1998 | Schwartz |
| 9 | U.S. Pat. No. 5,704,908 | Jan. 6, 1998 | Hoffman |
| 10 | U.S. Pat. No. 5,702,304 | Dec. 30, 1997 | Acres, et al. |
| 11 | U.S. Pat. No. 5,696,089 | Dec. 9, 1997 | Felix |
| 12 | U.S. Pat. No. 5,605,885 | Feb. 25, 1997 | Bernton |
| 13 | U.S. Pat. No. 5,486,505 | Jan. 23, 1996 | Bowers |
| 14 | U.S. Pat. No. 5,439,440 | Aug. 8, 1995 | Hoffman |
| 15 | U.S. Pat. No. 5,292,721 | Mar. 8, 1994 | Boyd |
| 16 | U.S. Pat. No. 5,137,872 | Aug. 11, 1992 | Seely |
| 17 | U.S. Pat. No. 5,134,120 | Jul. 28, 1992 | Boyd |
| 18 | U.S. Pat. No. 5,084,442 | Jan. 28, 1992 | Felix |
| 19 | U.S. Pat. No. 5,061,690 | Oct. 29, 1991 | Kann |
| 20 | U.S. Pat. No. 5,036,045 | Jul. 30, 1991 | Thorner |
| 21 | U.S. Pat. No. 5,023,322 | Jun. 11, 1991 | Kovacs |
| 22 | U.S. Pat. No. 4,956,288 | Sep. 11, 1990 | Barsoum |
| 23 | U.S. Pat. No. 4,839,344 | Jun. 13, 1989 | Bowers |
| 24 | U.S. Pat. No. 4,410,512 | Oct. 18, 1983 | Bowers |
| 25 | US-RE33,699 | Sep. 24, 1991 | Drengler |
| 26 | U.S. Pat. No. 4,833,166 | May 23, 1989 | Grosvenor |
| 27 | U.S. Pat. No. 4,228,158 | Oct. 14, 1980 | Momany |
| 28 | U.S. Pat. No. 4,228,156 | Oct. 14, 1980 | Momany |
| 29 | U.S. Pat. No. 4,226,857 | Oct. 7, 1980 | Momany |
| 30 | U.S. Pat. No. 4,224,316 | Sep. 23, 1980 | Momany |
| 31 | U.S. Pat. No. 4,223,021 | Sep. 16, 1980 | Momany |
| 32 | U.S. Pat. No. 4,223,020 | Sep. 16, 1980 | Momany |
| 33 | U.S. Pat. No. 4,223,019 | Sep. 16, 1980 | Momany |
| OTHER LITERATURE: | | | |
| 34 | PCT WO 96/12520 | | |
| 35 | PCT WO 96/12006 | | |
| 36 | PCT WO 95/19805 | | |
| 37 | PCT WO 97/07826 | | |

REFERENCE LIST

Acsadi, G., G. Dickson, D. R. Love, A. Jani, F. S. Walsh, A. Gurusinghe, Wolff, J A, and K. E. Davies. 1991. Human dystrophin expression in mdx mice after intramuscular injection of DNA constructs. Nature 352:815-818.

Aihara, H. and J. Miyazaki. 1998. Gene transfer into muscle by electroporation in vivo. Nat. Biotechnol. 16:867-870.

Aratani, Y., R. Okazaki, and H. Koyama. 1992. End extension repair of introduced targeting vectors mediated by homologous recombination in mammalian cells. Nucleic Acids Res. 20:4795-4801.

Bettan, M., F. Emmanuel, R. Darteil, J. M. Caillaud, F. Soubrier, P. Delaere, D. Branelec, A. Mahfoudi, N. Duverger, and D. Scherman. 2000. High-level protein secretion into blood circulation after electric pulse-mediated gene transfer into skeletal muscle. Mol. Ther. 2:204-210.

Butler, A. A., G. R. Ambler, B. H. Breier, D. LeRoith, C. T. Roberts, Jr., and P. D. Gluckman. 1994. Growth hormone (GH) and insulin-like growth factor-I (IGF-I) treatment of the GH-deficient dwarf rat: differential effects on IGF-I transcription start site expression in hepatic and extrahepatic tissues and lack of effect on type I IGF receptor mRNA expression. Mol. Cell Endocrinol. 101:321-330.

Caroni, P. and C. Schneider. 1994. Signaling by insulin-like growth factors in paralyzed skeletal muscle: rapid induction of IGF1 expression in muscle fibers and prevention of interstitial cell proliferation by IGF-BP5 and IGF-BP4. J. Neurosci. 14:3378-3388.

Corpas, E., S. M. Harman, M. A. Pineyro, R. Roberson, and M. R. Blackman. 1993. Continuous subcutaneous infusions of growth hormone (GH) releasing hormone 1-44 for 14 days increase GH and insulin-like growth factor-I levels in old men. Journal of Clinical Endocrinology & Metabolism 76:134-138.

Danko, I. and J. A. Wolff. 1994. Direct gene transfer into muscle. Vaccine 12:1499-1502.

Davis, H. L., R. G. Whalen, and B. A. Demeneix. 1993. Direct gene transfer into skeletal muscle in vivo: factors affecting efficiency of transfer and stability of expression. Human Gene Therapy 4:151-159.

Dolnik, V., M. Novotny, and J. Chmelik. 1993. Electromigration behavior of poly-(L-glutamate) conformers in concentrated polyacrylamide gels. Biopolymers 33:1299-1306.

Draghia-Akli, R., K. K. Cummings, A. S. Khan, P. A. Brown, and R. H. Carpenter. 2003a. Effects of plasmid-mediated growth hormone releasing hormone supplementation in young healthy Beagle dogs. Journal of Animal Science 81:2301-2310.

Draghia-Akli, R., K. M. Ellis, L. A. Hill, P. B. Malone, and M. L. Fiorotto. 2003b. High-efficiency growth hormone releasing hormone plasmid vector administration into skeletal muscle mediated by electroporation in pigs. FASEB J 17:526-528.

Draghia-Akli, R., M. L. Fiorotto, L. A. Hill, P. B. Malone, D. R. Deaver, and R. J. Schwartz. 1999. Myogenic expression of an injectable protease-resistant growth hormone-releasing hormone augments long-term growth in pigs. Nat. Biotechnol. 17:1179-1183.

Draghia-Akli, R., K. A. Hahn, G. K. King, K. Cummings, and R. H. Carpenter. 2002a. Effects Of Plasmid Mediated Growth Hormone Releasing Hormone In Severely Debilitated Dogs With Cancer. Molecular Therapy 6:830-836.

Draghia-Akli, R., A. S. Khan, K. K. Cummings, D. Parghi, R. H. Carpenter, and P. A. Brown. 2002b. Electrical Enhancement of Formulated Plasmid Delivery in Animals. Technology in Cancer Research & Treatment 1:365-371.

Draghia-Akli, R., X. G. Li, and R. J. Schwartz. 1997. Enhanced growth by ectopic expression of growth hormone releasing hormone using an injectable myogenic vector. Nat. Biotechnol. 15:1285-1289.

Draghia-Akli, R., P. B. Malone, L. A. Hill, K. M. Ellis, R. J. Schwartz, and J. L. Nordstrom. 2002c. Enhanced animal growth via ligand-regulated GHRH myogenic-injectable vectors. FASEB J. 16:426-428.

Dubreuil, P., D. Petitclerc, G. Pelletier, P. Gaudreau, C. Farmer, Mowles, T F, and P. Brazeau. 1990. Effect of dose and frequency of administration of a potent analog of human growth hormone-releasing factor on hormone secretion and growth in pigs. Journal of Animal Science 68:1254-1268.

Etherton, T. D., J. P. Wiggins, C. S. Chung, C. M. Evock, J. F. Rebhun, and P. E. Walton. 1986. Stimulation of pig growth performance by porcine growth hormone and growth hormone-releasing factor. Journal of Animal Science 63:1389-1399.

Fewell, J. G., F. MacLaughlin, V. Mehta, M. Gondo, F. Nicol, E. Wilson, and L. C. Smith. 2001. Gene therapy for the treatment of hemophilia B using PINC-formulated plasmid delivered to muscle with electroporation. Mol. Ther. 3:574-583.

Foncea, R., M. Andersson, A. Ketterman, V. Blakesley, M. Sapag-Hagar, P. H. Sugden, D. LeRoith, and S. Lavandero. 1997. Insulin-like growth factor-I rapidly activates multiple signal transduction pathways in cultured rat cardiac myocytes. J. Biol. Chem. 272:19115-19124.

Frohman, L. A., T. R. Downs, and P. Chomczynski. 1992. Regulation of growth hormone secretion. Frontiers in Neuroendocrinology 13:344-405.

Frohman, L. A., J. L. Thominet, C. B. Webb, M. L. Vance, H. Uderman, J. Rivier, W. Vale, and M. O. Thorner. 1984. Metabolic clearance and plasma disappearance rates of human pancreatic tumor growth hormone releasing factor in man. J. Clin. Invest. 73:1304-1311.

Fryer, A. D. and D. B. Jacoby. 1993. Effect of inflammatory cell mediators on M2 muscarinic receptors in the lungs. Life Sci. 52:529-536.

Gehl, J., T. Skovsgaard, and L. M. Mir. 1998. Enhancement of cytotoxicity by electropermeabilization: an improved method for screening drugs. Anticancer Drugs 9:319-325.

Gehl, J., T. H. Sorensen, K. Nielsen, P. Raskmark, S. L. Nielsen, T. Skovsgaard, and L. M. Mir. 1999. In vivo electroporation of skeletal muscle: threshold, efficacy and relation to electric field distribution. Biochim. Biophys. Acta 1428:233-240.

Gesundheit, N. and J. K. Alexander. 1995. Endocrine Therapy with Recombinant Hormones and Growth Factors. In: B. D. Weintraub (Ed.) Molecular Endocrinology: Basic Concepts and Clinical Correlations. pp. 491-507. Raven Press Ltd., New York.

Heller, R., M. J. Jaroszeski, L. F. Glass, J. L. Messina, D. P. Rapaport, R. C. DeConti, N. A. Fenske, R. A. Gilbert, L. M. Mir, and D. S. Reintgen. 1996. Phase I/II trial for the treatment of cutaneous and subcutaneous tumors using electrochemotherapy. Cancer 77:964-971.

Hoess, R. H. and K. Abremski. 1985. Mechanism of strand cleavage and exchange in the Cre-lox site-specific recombination system. J. Mol. Biol. 181:351-362.

Kooistra, H. S., G. Voorhout, J. A. Mol, and A. Rijnberk. 2000. Combined pituitary hormone deficiency in german shepherd dogs with dwarfism. Domest. Anim Endocrinol. 19:177-190.

Kooistra, H. S., G. Voorhout, P. J. Selman, and A. Rijnberk. 1998. Progestin-induced growth hormone (GH) production in the treatment of dogs with congenital GH deficiency. Domest. Anim Endocrinol. 15:93-102.

Lapierre, H., G. Pelletier, D. Petitclerc, P. Dubreuil, J. Morisset, P. Gaudreau, Y. Couture, and P. Brazeau. 1991. Effect of human growth hormone-releasing factor and(or) thyrotropin-releasing factor on growth, carcass composition, diet digestibility, nutrient balance, and plasma constituents in dairy calves. Journal of Animal Science 69:587-598.

Lesbordes, J. C., T. Bordet, G. Haase, L. Castelnau-Ptakhine, S. Rouhani, H. Gilgenkrantz, and A. Kahn. 2002. In vivo electrotransfer of the cardiotrophin-1 gene into skeletal muscle slows down progression of motor neuron degeneration in pmn mice. Hum. Mol. Genet. 11:1615-1625.

Li, C., S. Ke, Q. P. Wu, W. Tansey, N. Hunter, L. M. Buchmiller, L. Milas, C. Charnsangavej, and S. Wallace. 2000. Tumor irradiation enhances the tumor-specific distribution of poly(L-glutamic acid)-conjugated paclitaxel and its antitumor efficacy. Clin. Cancer Res. 6:2829-2834.

Li, X., E. M. Eastman, R. J. Schwartz, and R. Draghia-Akli. 1999. Synthetic muscle promoters: activities exceeding naturally occurring regulatory sequences. Nat. Biotechnol. 17:241-245.

Liu, J. L. and D. LeRoith. 1999. Insulin-like growth factor I is essential for postnatal growth in response to growth hormone. Endocrinology 140:5178-5184.

Lowe, W. L., Jr., M. Adamo, H. Werner, C. T. Roberts, Jr., and D. LeRoith. 1989. Regulation by fasting of rat insulin-like growth factor I and its receptor. Effects on gene expression and binding. J. Clin. Invest 84:619-626.

Lucas, M. L., L. Heller, D. Coppola, and R. Heller. 2002. IL-12 plasmid delivery by in vivo electroporation for the successful treatment of established subcutaneous B 16.F10 melanoma. Mol. Ther. 5:668-675.

Lucas, M. L., M. J. Jaroszeski, R. Gilbert, and R. Heller. 2001. In vivo electroporation using an exponentially enhanced pulse: a new waveform. DNA Cell Biol. 20:183-188.

Matsubara, H., Y. Gunji, T. Maeda, K. Tasaki, Y. Koide, T. Asano, T. Ochiai, S. Sakiyama, and M. Tagawa. 2001. Electroporation-mediated transfer of cytokine genes into human esophageal tumors produces anti-tumor effects in mice. Anticancer Res. 21:2501-2503.

Matsuo, A., I. Tooyama, S. Isobe, Y. Oomura, I. Akiguchi, K. Hanai, J. Kimura, and H. Kimura. 1994. Immunohistochemical localization in the rat brain of an epitope corresponding to the fibroblast growth factor receptor-1. Neuroscience 60:49-66.

McNally, M. A., J. S. Lebkowski, T. B. Okarma, and L. B. Lerch. 1988. Optimizing electroporation parameters for a variety of human hematopoietic cell lines. Biotechniques 6:882-886.

Miklavcic, D., K. Beravs, D. Semrov, M. Cemazar, F. Demsar, and G. Sersa. 1998. The importance of electric field distribution for effective in vivo electroporation of tissues. Biophys. J 74:2152-2158.

Mumper, R. J., J. Wang, S. L. Klakamp, H. Nitta, K. Anwer, F. Tagliaferri, and A. P. Rolland. 1998. Protective interactive noncondensing (PINC) polymers for enhanced plasmid distribution and expression in rat skeletal muscle. J. Control Release 52:191-203.

Muramatsu, T., S. Arakawa, K. Fukazawa, Y. Fujiwara, T. Yoshida, R. Sasaki, S. Masuda, and H. M. Park. 2001. In vivo gene electroporation in skeletal muscle with special reference to the duration of gene expression. Int. J Mol. Med. 7:37-42.

Nairn, R. S., G. M. Adair, T. Porter, S. L. Pennington, D. G. Smith, J. H. Wilson, and M. M. Seidman. 1993. Targeting vector configuration and method of gene transfer influence targeted correction of the APRT gene in Chinese hamster ovary cells. Somat. Cell Mol. Genet. 19:363-375.

Neumann, E., M. Schaefer-Ridder, Y. Wang, and P. H. Hofschneider. 1982. Gene transfer into mouse lyoma cells by electroporation in high electric fields. EMBO J. 1:841-845.

Otani, Y., Y. Tabata, and Y. Ikada. 1996. Rapidly curable biological glue composed of gelatin and poly(L-glutamic acid). Biomaterials 17:1387-1391.

Otani, Y., Y. Tabata, and Y. Ikada. 1998. Hemostatic capability of rapidly curable glues from gelatin, poly(L-glutamic acid), and carbodiimide. Biomaterials 19:2091-2098.

Parks, J. S., R. W. Pfaffle, M. R. Brown, H. Abdul-Latif, and L. R. Meacham. 1995. Growth Hormone Deficiency. In: B. D. Weintraub (Ed.) Molecular Endocrinology: Basic Concepts and Clinical Correlations. pp. 473-490. Raven Press,Ltd., New York.

Parrizas, M. and D. LeRoith. 1997. Insulin-like growth factor-1 inhibition of apoptosis is associated with increased expression of the bcl-xL gene product. Endocrinology 138:1355-1358.

Rabinovsky, E. D., G. M. Smith, D. P. Browder, H. D. Shine, and J. L. McManaman. 1992. Peripheral nerve injury down-regulates CNTF expression in adult rat sciatic nerves. J. Neurosci. Res. 31:188-192.

Rijnberk, A., H. van Herpen, J. A. Mol, and G. R. Rutteman. 1993. Disturbed release of growth hormone in mature dogs: a comparison with congenital growth hormone deficiency. Vet. Rec. 133:542-545.

Smith, L. C. and J. L. Nordstrom. 2000. Advances in plasmid gene delivery and expression in skeletal muscle. Curr. Opin. Mol. Ther. 2:150-154.

Terada, Y., H. Tanaka, T. Okado, S. Inoshita, M. Kuwahara, T. Akiba, S. Sasaki, and F. Marumo. 2001. Efficient and ligand-dependent regulated erythropoietin production by naked dna injection and in vivo electroporation. Am. J Kidney Dis. 38:S50-S53.

Thorner, M. O., L. A. Frohman, D. A. Leong, J. Thominet, T. Downs, P. Hellmann, J. Chitwood, J. M. Vaughan, and W. Vale. 1984. Extrahypothalamic growth-hormone-releasing factor (GRF) secretion is a rare cause of acromegaly: plasma GRF levels in 177 acromegalic patients. Journal of Clinical Endocrinology & Metabolism 59:846-849.

Toneguzzo, F., A. Keating, S. Glynn, and K. McDonald. 1988. Electric field-mediated gene transfer: characterization of DNA transfer and patterns of integration in lymphoid cells. Nucleic Acids Res. 16:5515-5532.

Tripathy, S. K., E. C. Svensson, H. B. Black, E. Goldwasser, M. Margalith, Hobart, P M, and J. M. Leiden. 1996. Long-term expression of erythropoietin in the systemic circulation of mice after intramuscular injection of a plasmid DNA vector. Proc. Natl. Acad. Sci. USA 93:10876-10880.

Tsurumi, Y., S. Takeshita, D. Chen, M. Kearney, S. T. Rossow, J. Passeri, J. R. Horowitz, J. F. Symes, and J. M.

Isner. 1996. Direct intramuscular gene transfer of naked DNA encoding vascular endothelial growth factor augments collateral development and tissue perfusion [see comments]. Circulation 94:3281-3290.

van Rooij, E. M., B. L. Haagmans, H. L. Glansbeek, Y. E. de Visser, M. G. de Bruin, W. Boersma, and A. T. Bianchi. 2000. A DNA vaccine coding for glycoprotein B of pseudorabies virus induces cell-mediated immunity in pigs and reduces virus excretion early after infection. Vet. Immunol. Immunopathol. 74:121-136.

Vance, M. L. 1990. Growth-hormone-releasing hormone. [Review] [52 refs]. Clinical Chemistry 36:415-420.

Vance, M. L., D. L. Kaiser, W. S. Evans, R. Furlanetto, W. Vale, J. Rivier, and M. O. Thorner. 1985. Pulsatile growth hormone secretion in normal man during a continuous 24-hour infusion of human growth hormone releasing factor (1-40). Evidence for intermittent somatostatin secretion. J. Clin. Invest. 75:1584-1590.

Veldhuis, J. D., A. Iranmanesh, and A. Weltman. 1997. ELEMENTS IN THE PATHOPHYSIOLOGY OF DIMINISHED GROWTH HORMONE (GH) SECRETION IN AGING HUMANS. Endocrine 7:41-48.

Vilquin, J. T., P. F. Kennel, M. Paturneau-Jouas, P. Chapdelaine, N. Boissel, P. Delaere, J. P. Tremblay, D. Scherman, M. Y. Fiszman, and K. Schwartz. 2001. Electrotransfer of naked DNA in the skeletal muscles of animal models of muscular dystrophies. Gene Ther. 8:1097-1107.

Wolff, J. A., R. W. Malone, P. Williams, W. Chong, G. Acsadi, A. Jani, Felgner, and PL. 1990. Direct gene transfer into mouse muscle in vivo. Science 247:1465-1468.

Xie, T. D. and T. Y. Tsong. 1993. Study of mechanisms of electric field-induced DNA transfection. V. Effects of DNA topology on surface binding, cell uptake, expression, and integration into host chromosomes of DNA in the mammalian cell. Biophys. J. 65:1684-1689.

Yasui, A., K. Oda, H. Usunomiya, K. Kakudo, T. Suzuki, T. Yoshida, H. M. Park, K. Fukazawa, and T. Muramatsu. 2001. Elevated gastrin secretion by in vivo gene electroporation in skeletal muscle. Int. J Mol. Med. 8:489-494.

Yin, D. and J. G. Tang. 2001. Gene therapy for streptozotocin-induced diabetic mice by electroporational transfer of naked human insulin precursor DNA into skeletal muscle in vivo. FEBS Lett. 495:16-20.

Yorifuji, T. and H. Mikawa. 1990. Co-transfer of restriction endonucleases and plasmid DNA into mammalian cells by electroporation: effects on stable transformation. Mutat. Res. 243:121-126.

---

What is claimed is:

1. A composition comprising a nucleic acid expression construct that encodes the canine specific growth hormone releasing hormone ("dGHRH") consisting of SEQ ID NO.: 04.

2. The composition of claim 1, wherein the dGHRH increases growth hormone ("GH") in a recipient subject.

3. The composition of claim 1, wherein the dGHRH improves hematological parameters in a recipient subject.

4. The composition of claim 1, wherein the dGHRH increases red blood cell values in a recipient subject.

5. The composition of claim 1, wherein the dGHRH increases hemoglobin values in a recipient subject.

6. The composition of claim 1, wherein the dGHRH increases mean corpuscular hemoglobin values in a recipient subject.

7. The composition of claim 1, wherein the nucleic acid expression construct further comprises:

I. a synthetic or eukaryotic promoter;
II. a poly-adenylation signal;
III. a selectable marker gene promoter;
IV. a ribosomal binding site;
V. a selectable marker gene sequence; and
VI. an origin of replication.

8. The composition of claim 7, wherein the polyadenylation signal comprises a portion of the human growth hormone 3'-untranslated region.

9. A composition comprising a nucleic acid expression construct that encodes the canine specific growth hormone releasing hormone consisting of SEQ ID NO.:03.

* * * * *

SEQUENCE LISTING

```
<160> NUMBER OF SEQ ID NOS: 16

<210> SEQ ID NO 1
<211> LENGTH: 40
<212> TYPE: PRT
<213> ORGANISM: Artificial sequence
<220> FEATURE:
<223> OTHER INFORMATION: This is the amino acid sequence for porcine
      GHRH.

<400> SEQUENCE: 1

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Gln Glu Gln Gly Ala
        35                  40

<210> SEQ ID NO 2
<211> LENGTH: 40
<212> TYPE: PRT
<213> ORGANISM: artificial sequence
<220> FEATURE:
<223> OTHER INFORMATION: This is a modified amino acid sequence for
      GHRH

<400> SEQUENCE: 2

His Val Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 3
<211> LENGTH: 40
```

```
<212> TYPE: PRT
<213> ORGANISM: artificial sequence
<220> FEATURE:
<223> OTHER INFORMATION: This is the amino acid sequence for canine
      GHRH.

<400> SEQUENCE: 3

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Arg Glu Gln Gly Ala
        35                  40

<210> SEQ ID NO 4
<211> LENGTH: 40
<212> TYPE: PRT
<213> ORGANISM: artificial sequence
<220> FEATURE:
<223> OTHER INFORMATION: This is the general amino acid sequence for
      canine GHRH.
<220> FEATURE:
<221> NAME/KEY: MISC_FEATURE
<222> LOCATION: (1)..(1)
<223> OTHER INFORMATION: Xaa at position 1 may be tyrosine, or histidine
<220> FEATURE:
<221> NAME/KEY: MISC_FEATURE
<222> LOCATION: (2)..(2)
<223> OTHER INFORMATION: Xaa at position 2 may be alanine, valine, or
      isoleucine.
<220> FEATURE:
<221> NAME/KEY: MISC_FEATURE
<222> LOCATION: (15)..(15)
<223> OTHER INFORMATION: Xaa at position 15 may be alanine, valine, or
      isoleucine.
<220> FEATURE:
<221> NAME/KEY: MISC_FEATURE
<222> LOCATION: (27)..(27)
<223> OTHER INFORMATION: Xaa at position 27 may be methionine, or
      leucine.
<220> FEATURE:
<221> NAME/KEY: MISC_FEATURE
<222> LOCATION: (28)..(28)
<223> OTHER INFORMATION: Xaa at position 28 may be serine or asparagine.

<400> SEQUENCE: 4

Xaa Xaa Asp Ala Ile Phe Thr Asn Ser Tyr Arg Lys Val Leu Xaa Gln
1               5                   10                  15

Leu Ser Ala Arg Lys Leu Leu Gln Asp Ile Xaa Xaa Arg Gln Gln Gly
            20                  25                  30

Glu Arg Asn Arg Glu Gln Gly Ala
        35                  40

<210> SEQ ID NO 5
<211> LENGTH: 2716
<212> TYPE: DNA
<213> ORGANISM: Artificial Sequence
<220> FEATURE:
<223> OTHER INFORMATION: pAV0221 is an expression plasmid having a dGHRH
      sequence.

<400> SEQUENCE: 5
ccaccgcggt ggcggccgtc cgccctcggc accatcctca cgacacccaa atatggcgac      60
gggtgaggaa tggtggggag ttattttttag agcggtgagg aaggtgggca ggcagcaggt    120
gttggcgctc taaaataac tcccgggagt tattttaga gcggaggaat ggtggacacc      180
caaatatggc gacggttcct caccgtcgc catatttggg tgtccgccct cggccggggc     240
```

```
cgcattcctg ggggccgggc ggtgctcccg cccgcctcga taaaaggctc cggggccggc    300
ggcggcccac gagctacccg gaggagcggg aggcgccaag cggatcccaa ggcccaactc    360
cccgaaccac tcagggtcct gtggacagct cacctagctg ccatggtgct ctgggtgttc    420
ttcctggtga tcctcaccct cagcagtggt tcccactctt ccccgccatc cctgcccatc    480
agaatccctc ggtatgcaga cgccatcttc accaacagct accggaaggt gctgggccag    540
ctgtccgccc gcaagctcct scaggacatc atgagccggc agcagggaga gagaaaccgg    600
gagcaaggag catagtaagc ttatcggggt ggcatccctg tgaccccctcc ccagtgcctc    660 tcctggccct ggaagttgcc actccagtgc ccaccagcct tgtcctaata aaattaagtt    720
gcatcatttt gtctgactag gtgtccttct ataatattat ggggtggagg ggggtggtat    780
ggagcaaggg gcaagttggg aagacaacct gtagggctcg aggggggggcc cggtaccagc    840 ttttgttccc tttagtgagg gttaatttcg agcttggtct tccgcttcct cgctcactga    900
ctcgctgcgc tcgtcgttc ggctgcggcg agcggtatca gctcactcaa aggcggtaat    960
acggttatcc acagaatcag gggataacgc aggaaagaac atgtgagcaa aaggccagca   1020
aaaggccagg aaccgtaaaa aggccgcgtt gctggcgttt ttccataggc tccgcccccc   1080
tgacgagcat cacaaaaatc gacgctcaag tcagaggtgg cgaaacccga caggactata   1140
aagataccag gcgtttcccc ctggaagctc cctcgtgcgc tctcctgttc cgaccctgcc   1200
gcttaccgga tacctgtccg cctttctccc ttcgggaagc gtggcgcttt ctcatagctc   1260
acgctgtagg tatctcagtt cggtgtaggt cgttcgctcc aagctgggct gtgtgcacga   1320
accccccgtt cagcccgacc gctgcgcctt atccggtaac tatcgtcttg agtccaaccc   1380
ggtaagacac gacttatcgc cactggcagc agccactggt aacaggatta gcagagcgag   1440
gtatgtaggc ggtgctacag agttcttgaa gtggtggcct aactacggct acactagaag   1500
aacagtattt ggtatctgcg ctctgctgaa gccagttacc ttcggaaaaa gagttggtag   1560
ctcttgatcc ggcaaacaaa ccaccgctgg tagcggtggt ttttttgttt gcaagcagca   1620
gattacgcgc agaaaaaaag gatctcaaga agatcctttg atcttttcta cggggtctga   1680
cgctcagcta gcgctcagaa gaactcgtca agaaggcgat agaaggcgat gcgctgcgaa   1740
tcgggagcgg cgataccgta aagcacgagg aagcggtcag cccattcgcc gccaagctct   1800
tcagcaatat cacgggtagc caacgctatg tcctgatagc ggtccgccac acccagccgg   1860
ccacagtcga tgaatccaga aaagcggcca ttttccacca tgatattcgg caagcaggca   1920
tcgccatgag tcacgacgag atcctcgccg tcgggcatgc gcgccttgag cctggcgaac   1980
agttcggctg gcgcgagccc ctgatgctct tcgtccagat catcctgatc gacaagaccg   2040
gcttccatcc gagtacgtgc tcgctcgatg cgatgtttcg cttggtggtc gaatgggcag   2100
gtagccggat caagcgtatg cagccgccgc attgcatcag ccatgatgga ctttctctcg   2160
gcaggagcaa ggtgagatga caggagatcc tgccccggca cttcgcccaa tagcagccag   2220
tcccttcccg cttcagtgac aacgtcgagc acagctgcgc aaggaacgcc cgtcgtggcc   2280
agccacgata gccgcgctgc ctcgtcctgc agttcattca gggcaccgga caggtcggtc   2340
ttgacaaaaa gaaccgggcg cccctgcgct gacagccgga acacggcggc atcagagcag   2400
ccgattgtct gttgtgccca gtcatagccg aatagcctct ccacccaagc ggccggagaa   2460
cctgcgtgca atccatcttg ttcaatcatg cgaaacgatc ctcatcctgt ctcttgatca   2520
gatcttgatc ccctgcgcca tcagatcctt ggcggcaaga aagccatcca gtttactttg   2580
cagggcttcc caaccttacc agagggcgcc ccagctggca attccggttc gcttgctgtc   2640
```

```
cataaaaccg cccagtctag caactgttgg gaagggcgat cgtgtaatac gactcactat    2700
agggcgaatt ggagct                                                    2716

<210> SEQ ID NO 6
<211> LENGTH: 2739
<212> TYPE: DNA
<213> ORGANISM: Artificial Sequence
<220> FEATURE:
<223> OTHER INFORMATION: pAV0215 is an expression plasmid for HV-GHRH.

<400> SEQUENCE: 6
ccaccgcggt ggcggccgtc cgccctcggc accatcctca cgacacccaa atatggcgac      60
gggtgaggaa tggtggggag ttattttag agcggtgagg aaggtgggca ggcagcaggt     120
gttggcgctc taaaaataac tcccgggagt tatttttaga gcggaggaat ggtggacacc     180
caaatatggc gacggttcct cacccgtcgc catatttggg tgtccgccct cggccggggc     240
cgcattcctg ggggccgggc ggtgctcccg cccgcctcga taaaaggctc cggggccggc     300
ggcggcccac gagctacccg gaggagcggg aggcgccaag cggatcccaa ggcccaactc     360
cccgaaccac tcagggtcct gtggacagct cacctagctg ccatggtgct ctgggtgttc     420
ttctttgtga tcctcaccct cagcaacagc tcccactgct ccccacctcc ccctttgacc     480
ctcaggatgc ggcggcacgt agatgccatc ttcaccaaca gctaccggaa ggtgctggcc     540
cagctgtccg cccgcaagct gctccaggac atcctgaaca ggcagcaggg agagaggaac     600
caagagcaag gagcataatg actgcaggaa ttcgatatca agcttatcgg ggtggcatcc     660
ctgtgacccc tccccagtgc ctctcctggc cctggaagtt gccactccag tgcccaccag     720
ccttgtccta ataaaattaa gttgcatcat tttgtctgac taggtgtcct tctataatat     780
tatggggtgg aggggggtgg tatggagcaa ggggcaagtt gggaagacaa cctgtagggc     840 tcgaggggggg gcccggtacc agcttttgtt cccttttagtg agggttaatt tcgagcttgg     900
tcttccgctt cctcgctcac tgactcgctg cgctcggtcg ttcggctgcg gcgagcggta     960
tcagctcact caaaggcggt aatacggtta tccacagaat caggggataa cgcaggaaag    1020
aacatgtgag caaaaggcca gcaaaaggcc aggaaccgta aaaaggccgc gttgctggcg    1080 ttttttccata ggctccgccc ccctgacgag catcacaaaa atcgacgctc aagtcagagg    1140
tggcgaaacc cgacaggact ataaagatac caggcgtttc cccctggaag ctccctcgtg    1200
cgctctcctg ttccgaccct gccgcttacc ggatacctgt ccgcctttct cccttcggga    1260
agcgtggcgc tttctcatag ctcacgctgt aggtatctca gttcggtgta ggtcgttcgc    1320
tccaagctgg gctgtgtgca cgaaccccc gttcagcccg accgctgcgc cttatccggt    1380
aactatcgtc ttgagtccaa cccggtaaga cacgacttat cgccactggc agcagccact    1440
ggtaacagga ttagcagagc gaggtatgta ggcggtgcta cagagttctt gaagtggtgg    1500
cctaactacg gctacactag aagaacagta tttggtatct gcgctctgct gaagccagtt    1560
accttcggaa aaagagttgg tagctcttga tccggcaaac aaaccaccgc tggtagcggt    1620
ggtttttttg tttgcaagca gcagattacg cgcagaaaaa aaggatctca agaagatcct    1680
ttgatctttt ctacggggtc tgacgctcag ctagcgctca aagaactcg tcaagaaggc    1740 gatagaaggc gatgcgctgc gaatcgggag cggcgatacc gtaaagcacg aggaagcggt    1800
cagcccattc gccgccaagc tcttcagcaa tatcacgggt agccaacgct atgtcctgat    1860
agcggtccgc cacacccagc cggccacagt cgatgaatcc agaaaagcgg ccattttcca    1920
```

```
ccatgatatt cggcaagcag gcatcgccat gagtcacgac gagatcctcg ccgtcgggca    1980
tgcgcgcctt gagcctggcg aacagttcgg ctggcgcgag ccctgatgc tcttcgtcca    2040 gatcatcctg atcgacaaga ccggcttcca tccgagtacg tgctcgctcg atgcgatgtt    2100
tcgcttggtg gtcgaatggg caggtagccg gatcaagcgt atgcagccgc cgcattgcat    2160
cagccatgat ggatactttc tcggcaggag caaggtgaga tgacaggaga tcctgccccg    2220
gcacttcgcc caatagcagc cagtcccttc ccgcttcagt gacaacgtcg agcacagctg    2280
cgcaaggaac gcccgtcgtg gccagccacg atagccgcgc tgcctcgtcc tgcagttcat    2340
tcagggcacc ggacaggtcg gtcttgacaa aaagaaccgg gcgcccctgc gctgacagcc    2400
ggaacacggc ggcatcagag cagccgattg tctgttgtgc ccagtcatag ccgaatagcc    2460
tctccaccca agcggccgga gaacctgcgt gcaatccatc ttgttcaatc atgcgaaacg    2520
atcctcatcc tgtctcttga tcagatcttg atcccctgcg ccatcagatc cttggcggca    2580
agaaagccat ccagtttact ttgcagggct tcccaacctt accagagggc gccccagctg    2640
gcaattccgg ttcgcttgct gtccataaaa ccgcccagtc tagcaactgt tgggaagggc    2700
gatcgtgtaa tacgactcac tatagggcga attggagct                          2739

<210> SEQ ID NO 7
<211> LENGTH: 20
<212> TYPE: DNA
<213> ORGANISM: artificial sequence
<220> FEATURE:
<223> OTHER INFORMATION: A 5' primer selected from the Bam/Hind III
      fragment of HV-GHRH.

<400> SEQUENCE: 7
atggtgctct gggtgttctt                                                 20

<210> SEQ ID NO 8
<211> LENGTH: 20
<212> TYPE: DNA
<213> ORGANISM: artificial sequence
<220> FEATURE:
<223> OTHER INFORMATION: A 3' primer selected from sequence in Exon 5 of
      bovine GHRH.

<400> SEQUENCE: 8
ttcatccttg ggagttcctg                                                 20

<210> SEQ ID NO 9
<211> LENGTH: 24
<212> TYPE: DNA
<213> ORGANISM: artificial sequence
<220> FEATURE:
<223> OTHER INFORMATION: a Primer designed with specific mutations

<400> SEQUENCE: 9
cggccgaaag cttactatgc tcct                                            24

<210> SEQ ID NO 10
<211> LENGTH: 23
<212> TYPE: DNA
<213> ORGANISM: artificial sequence
<220> FEATURE:
<223> OTHER INFORMATION: a Primer designed with specific mutations

<400> SEQUENCE: 10
attcgccccc atggtgctct ggg                                             23
```

<210> SEQ ID NO 11
<211> LENGTH: 323
<212> TYPE: DNA
<213> ORGANISM: artificial sequence
<220> FEATURE:
<223> OTHER INFORMATION: Nucleic acid sequence of a synthetic eukaryotic promoter SPc5-12

<400> SEQUENCE: 11

```
cggccgtccg ccctcggcac catcctcacg acacccaaat atggcgacgg gtgaggaatg      60
gtggggagtt atttttagag cggtgaggaa ggtgggcagg cagcaggtgt tggcgctcta     120
aaaataactc ccgggagtta tttttagagc ggaggaatgg tggacaccca aatatggcga     180
cggttcctca cccgtcgcca tatttgggtg tccgccctcg gccggggccg cattcctggg     240
ggccgggcgg tgctcccgcc cgcctcgata aaaggctccg gggccggcgg cggcccacga     300
gctacccgga ggagcgggag gcg                                             323
```

<210> SEQ ID NO 12
<211> LENGTH: 190
<212> TYPE: DNA
<213> ORGANISM: artificial sequence
<220> FEATURE:
<223> OTHER INFORMATION: Nucleic acid sequence of a human growth hormone poly A tail.

<400> SEQUENCE: 12

```
gggtggcatc cctgtgaccc ctccccagtg cctctcctgg ccctggaagt tgccactcca      60
gtgcccacca gccttgtcct aataaaatta agttgcatca ttttgtctga ctaggtgtcc     120
ttctataata ttatggggtg gagggggtg gtatggagca aggggcaagt tgggaagaca     180
acctgtaggg                                                            190
```

<210> SEQ ID NO 13
<211> LENGTH: 29
<212> TYPE: DNA
<213> ORGANISM: Artificial Sequence
<220> FEATURE:
<223> OTHER INFORMATION: Prokaryotic selectable marker gene promoter PNEO.

<400> SEQUENCE: 13

```
accttaccag agggcgcccc agctggcaa                                        29
```

<210> SEQ ID NO 14
<211> LENGTH: 5
<212> TYPE: DNA
<213> ORGANISM: artificial sequence
<220> FEATURE:
<223> OTHER INFORMATION: NEO ribosomal binding site.

<400> SEQUENCE: 14

```
tcctc                                                                   5
```

<210> SEQ ID NO 15
<211> LENGTH: 795
<212> TYPE: DNA
<213> ORGANISM: artificial sequence
<220> FEATURE:
<223> OTHER INFORMATION: Sequence for antibiotic resistance gene kanamycin.

<400> SEQUENCE: 15

```
atgattgaac aagatggatt gcacgcaggt tctccggccg cttgggtgga gaggctattc      60
```

-continued

```
ggctatgact gggcacaaca gacaatcggc tgctctgatg ccgccgtgtt ccggctgtca    120 gcgcagggc gcccggttct ttttgtcaag accgacctgt ccggtgccct gaatgaactg    180
caggacgagg cagcgcggct atcgtggctg gccacgacgg gcgttccttg cgcagctgtg    240
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgaggatc tcgtcgtgac tcatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                     795
```

<210> SEQ ID NO 16
<211> LENGTH: 782
<212> TYPE: DNA
<213> ORGANISM: artificial sequence
<220> FEATURE:
<223> OTHER INFORMATION: Sequence of a plasmid pUC-18 origin of replication.

<400> SEQUENCE: 16

```
tcttccgctt cctcgctcac tgactcgctg cgctcggtcg ttcggctgcg gcgagcggta     60
tcagctcact caaaggcggt aatacggtta tccacagaat caggggataa cgcaggaaag    120
aacatgtgag caaaaggcca gcaaaaggcc aggaaccgta aaaaggccgc gttgctggcg    180
tttttccata ggctccgccc ccctgacgag catcacaaaa atcgacgctc aagtcagagg    240
tggcgaaacc cgacaggact ataaagatac caggcgtttc ccctggaag ctccctcgtg    300 cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaaccccc gttcagcccg accgctgcgc cttatccggt    480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aaggacagta tttggtatct gcgctctgct gaagccagtt    660
accttcggaa aaagagttgg tagctcttga tccggcaaac aaaccaccgc tggtagcggt    720 ggttttttg tttgcaagca gcagattacg cgcagaaaaa aaggatctca agaagatcct    780
tt                                                                    782
```